US007312195B2

(12) United States Patent
Craik et al.

(10) Patent No.: US 7,312,195 B2
(45) Date of Patent: *Dec. 25, 2007

(54) CYCLISED CONOTOXIN PEPTIDES

(75) Inventors: David James Craik, Chapel Hill (AU); Norelle Lee Daly, Kenmore (AU); Katherine Justine Nielsen, Chapel Hill (AU); Christopher John Armishaw, Hellerup (DK); Richard Clark, Chapel Hill (AU); Paul Francis Alewood, Pullenvale (AU)

(73) Assignee: The University of Queensland, Queensland (AU)

(*) Notice: Subject to any disclaimer, the term of this patent is extended or adjusted under 35 U.S.C. 154(b) by 0 days.

This patent is subject to a terminal disclaimer.

(21) Appl. No.: 11/052,168

(22) Filed: Feb. 7, 2005

(65) Prior Publication Data
US 2005/0256301 A1 Nov. 17, 2005

Related U.S. Application Data

(63) Continuation-in-part of application No. 09/787,082, filed as application No. PCT/AU99/00769 on Sep. 14, 1999, now Pat. No. 7,001,883.

(30) Foreign Application Priority Data
Sep. 14, 1998 (AU) .................................. PP5895

(51) Int. Cl.
A61K 38/12 (2006.01)
C07K 14/00 (2006.01)
(52) U.S. Cl. .............................. 514/9; 514/12; 514/13; 514/21; 530/317; 530/324; 530/326; 530/334; 530/344; 424/9.1
(58) Field of Classification Search .................... 514/9, 514/12, 13, 21; 530/317, 324, 326, 334, 530/344; 424/9.1
See application file for complete search history.

(56) References Cited

U.S. PATENT DOCUMENTS

| 4,447,356 A | 5/1984 | Olivera et al. ............... 530/327 |
| 5,589,356 A | 12/1996 | Tam ........................... 435/68.1 |
| 7,001,883 B1 * | 2/2006 | Craik et al. ..................... 514/9 |

FOREIGN PATENT DOCUMENTS

| WO | WO 96/33206 | 10/1996 |
| WO | WO-96/33206 | * 10/1996 |
| WO | WO 96/34878 | 11/1996 |
| WO | WO 98/03541 | 1/1998 |
| WO | WO 98/20026 | 5/1998 |
| WO | WO 98/28434 | 7/1998 |
| WO | WO 98/56807 | 12/1998 |

OTHER PUBLICATIONS

Armishaw et al., American Peptide Society, pp. 113-114, 2001.*
Al-Obeidi, F., et al., "Potent and prolonged acting cyclic lactam analogues of α-melanotropin: design based on molecular dynamics," *J. Med. Chem.*, 1989, 32, 2555-2561.
Armishaw, C.J., et al., "Synthesis of backbone cyclic analogues of α-conotoxin IMI by chemoselective ligation of unprotected linear precursors," Benedetti, E., et al. (Eds.), *Peptides*, 2002, 1 page (Abstract).
Armishaw C.J., et al., "Synthesis of N to C terminal cyclic analogues of α-conotoxin ImI by chemoselective ligation of unprotected linear precursors," *Peptides: The Wave of the Future*, Lebl, M., et al. (Eds.), *American Peptide Society*, 2001, 113-114.
Botti, P., et al., "Cyclic peptides from linear unprotected peptide precursors through thiazolidine formation," *J. Am. Chem. Soc.*, 1996, 118, 10018-10024.
Byk, G., et al., "Synthesis and biological activity of NK-1 selective, N-backbone cyclic analogs of the C-terminal hexapeptide of substance P," *J. Med. Chem.*, 1996, 39, 3174-3178.
Charpentier, B., et al., "Synthesis and binding affinities of cyclic and related linear analogues of $CCK_8$ selective for central receptors," *J. Med. Chem.*, 1989, 32, 1184-1190.
Chazin, W.J., et al., "Comparative studies of conformation and internal mobility in native and circular basic pancreatic trypsin inhibitor by $^1H$ nuclear magnetic resonance in solution," *Eur. J. Biochem.*, 1985, 152, 429-437.
Chu, V., et al., "Thermodynamic and structural consequences of flexible loop deletion by circular permutation in the streptavidin-biotin system," *Protein Science*, 1998, 7, 848-859.
Claeson, P., et al., "Fractionation protocol for the isolation of polypeptides from plant biomass," *J. Nat. Prod.*, 1998, 61, 77-81.
Feng, Y., et al., "Circular permutation of granulocyte colony-stimulating factor," *Biochemistry*, 1999, 38, 4553-4563.
Garrett, J.B., et al., "Are turns required for the folding of ribonuclease T1?," *Protein Science*, 1996, 5, 204-211.
Gilon, C., et al., "Backbone cyclization: a new method for conferring conformational constraint on peptides," *Biopolymers*, 1991, 31, 745-750.
Goldenberg, D.P., et al., "Circular and circularly permuted forms of bovine pancreatic trypsin inhibitor," *J. Mol. Biol.*, 1983, 165, 407-413.
Goldenberg, D.P., et al., "Folding pathway of a circular form of bovine pancreatic trysin inhibitor," *J. Mol. Biol.*, 1984, 179, 527-545.
Goldenberg, D.P., "Dissecting the roles of individual interactions in protein stability: lessons from a circularized protein," *J. Cellular Biochemistry*, 1985, 29, 321-335.
Gray, W.R., et al., "Conotoxin MI—Disulfide bonding and conformational states," *J. Biological Chemistry*, Oct. 25, 1983, 258(20), 12247-12251.
Gutknecht, R., et al., "The glucose transporter of *Escherichia coli* with circularly permuted domains is active in vivo and in vitro," *J. Biological Chemistry*, Oct. 2, 1998, 273(40), 25745-25750.
Hennecke, J., et al., "Conversion of a catalytic into a structural disulfide bond by circular permutation," *Biochemistry*, 1998, 37, 17590-17597.

(Continued)

Primary Examiner—Chih-Min Kam
(74) Attorney, Agent, or Firm—Woodcock Washburn LLP

(57) ABSTRACT

This invention relates to cyclised conotoxin peptides, processes for their preparation and their pharmaceutical use.

OTHER PUBLICATIONS

Hruby, V.J., "Design of peptide hormone and neurotransmitter analogues," *TIPS*, Jun. 1985, 259-262.

Hruby, V.J., "Conformational restrictions of biologically active peptides via amino acid side chain groups," *Life Sciences*, 1982, 31(3), 189-199.

Jackson, D.Y., et al., "Enzymatic cyclization of linear peptide esters using subtiligase," *J. Am. Chem. Soc.*, 1995, 117, 819-820.

Jacobsen, R.B., et al., "A novel D-leucine-containing *conus* peptide: diverse conformational dynamics in the contryphan family," *J. Peptide Res.*, 1999, 54, 93-99.

Kreitman, R.J., "A circularly permuted recombinant interleukin 4 toxin with increased activity," *Proc. Natl. Acad. Sci. USA*, Jul. 1994, 91, 6889-6893.

Kreitman, R.J., et al., "Increased antitumor activity of a circularly permuted interleukin 4-toxin in mice with interleukin 4 receptor-bearing human carcinoma," *Cancer Research*, Aug. 1, 1995, 3357-3363.

Lender, A., et al., "Design and synthesis of sulfur-free cyclic hexapeptides which contain the RGD sequence and bind to the fibrinogen GP IIb/IIIa," *Int. J. Peptide Protein Res.*, 1993, 42, 509-517.

Muir, T.W., et al., "Expressed protein ligation: a general method for protein engineering," *Proc. Natl. Acad. Sci. USA*, Jun. 1998, 95, 6705-6710.

Myers, R.A., et al., "*Conus* peptides as chemical probes for receptors and ion channels," *Chem. Rev.*, 1993, 93, 1923-1936.

Okumu, F.W., et al., "Effect of restricted conformational flexibility on the permeation of model hexapeptides across caco-2 cell monolayers," *Pharmaceutical Res.*, 1997, 14(2), 169-175.

Olivera, B.M., et al., "Minireview: Conotoxins," *J. Biological Chemistry*, Nov. 25, 1991, 266(33), 22067-22070.

Olivera, B.M., "Diversity of *Conus* neuropeptides," *Science*, Jul. 20, 1990, 249, 257-250.

Pallaghy, P.K., et al., "A common structural motif incorporating a cystine knot and a triple-stranded β-sheet in toxic and inhibitory polypeptides," *Protein Science*, 1994, 3, 1833-1839.

Rivier, J.E., et al., "Bicyclic gonadotropin releasing hormone (GnRH) antagonists," *Peptides Chemistry, Structure and Biology*, 1990, 33-37.

Rote, K.V., et al., "Circular pancreatic trypsin inhibitor: A novel substrate for studies on intracellular proteolysis," *J. Biological Chemistry*, Jan. 15, 1989, 264(2), 1156-1162.

Saether, O., et al., "Elucidation of the primary and three-dimensional structure of the uterotonic polypeptide kalata B1," *Biochemistry*, 1995, 34, 4147-4158.

Tam, J.P., et al., "Thia zip reaction for synthesis of large cyclic peptides: mechanisms and applications," *J. Am. Chem. Soc.*, 1999, 121, 4316-4324.

Tam, J.P., et al., "Synthesis of large cyclic cystine-knot peptide by orthogonal coupling strategy using unprotected peptide precursor," *Tetrahedron Letters*, 1997, 38(32), 5599-5602.

Tam, J.P., "A biomimetic strategy in the synthesis and fragmentation of cyclic protein," *Protein Science*, 1998, 7, 1583-1592.

Terada, S., et al., "Synthesis and hydrolysis by pepsin and trypsin of a cyclic hexapeptide containing lysine and phenylalanine," *Eur. J. Biochem.*, 1975, 52, 273-282.

Wieligmann, K., et al., "Eye lens βB2-crystallin: circular permutation does not influence the oligomerization state but enhances the conformational stability," *J. Mol. Biol.*, 1998, 280, 721-729.

Zhang, L., et al., "Synthesis and application of unprotected cyclic peptides as building blocks for peptide dendrimers," *J. Am. Chem. Soc.*, 1997, 119, 2363-2370.

\* cited by examiner

PVIIA

MVIIA

GS

CYCLISED CONOTOXIN PEPTIDES

This application is a continuation-in-part of U.S. application Ser. No. 09/787,082 filed Jun. 14, 2001, now U.S. Pat. No. 7,001,883, which is the U.S. National Phase under 35 U.S.C. 371 of International Application PCT/AU 99/00769 filed Sep. 14, 1999 which claims priority to Australian Application PP 5895 filed Sep. 14, 1998.

This invention relates to novel peptides and derivatives thereof, in particular to a range of cyclised peptides useful in the therapeutic treatment of humans. The invention also relates to pharmaceutical compositions comprising these peptides, methods for making the peptides and the use of these peptides in the prophylaxis or treatment of conditions or diseases in humans.

The marine snails of the genus *Conus* (cone snails) use a sophisticated biochemical strategy to capture their prey. As predators of either fish, worms or other molluscs, the cone snails inject their prey with venom containing a cocktail of small bioactive peptides. These toxin molecules, which are referred to as conotoxins, interfere with neurotransmission by targeting a variety of receptors and ion-channels. They typically contain 12-30 amino acids arranged in linear sequence. The venom from any single *Conus* species may contain more than 100 different peptides. The conotoxins are divided into classes on the basis of their physiological targets. To date, at least ten classes have been described. The (ω-conotoxin class of peptides target and block voltage-sensitive $Ca^{2+}$-channels inhibiting neurotransmitter release. The α-conotoxins and ψ-conotoxins target and block nicotinic ACh receptors, causing ganglionic and neuromuscular blockade. Peptides of the μ-conotoxin class act on voltage-sensitive $Na^+$-channels and block muscle and nerve action potentials. The δ-conotoxins target and delay the inactivation of voltage-sensitive $Na^+$-channels enhancing neuronal excitability. The κ-conotoxin class of peptides target and block voltage-sensitive $K^+$-channels, and these may also cause enhanced neuronal excitability. The conopressins are vasopressin receptor antagonists and the conantokins are NMDA receptor antagonists. The prototype of a new γ-conotoxin class has also been described which targets a voltage-sensitive nonspecific cation channel. More recently, a new σ-conotoxin class, which antagonises the $5HT_3$ receptor, a new χ-conotoxin class, which inhibits neuronal amine transporter and a new ρ-conotoxin class, which inhibits $α_1$ adrenergic receptors, have been described.

Most conotoxin peptides contain either four (4) or six (6) cysteine residues which are bonded in pairs to form either two (2) or three (3) disulfide bonds respectively, although there are some examples having two cysteine residues bonded to form a single disulfide bond (ie., conopressins), as well as some having greater than three disulfide bonds. The peptides of some of the "activity" classes described above share a structural motif, possessing the same number of cysteine residues and the same disulfide bond connectivity. Accordingly a new "superfamily" classification system has been developed. For example, the ω-conotoxins and members of the κ-, δ- and μ-conotoxin classes have six cysteine residues which are bonded in pairs to form three disulfide bonds between cysteine residues 1-4, 2-5 and 3-6. Conotoxin peptides having this structural motif belong to the "O-superfamily" ofconotoxins. Similarly ρ-conotoxins and most α-conotoxins have four cysteine residues bonded in pairs to form two disulfide bonds between cysteine residues 1-3 and 2-4. These conotoxin peptides belong to the "A-superfamily" of conotoxins. The χ-conotoxins also have four cysteine residues bonded in pairs to form two disulfide bonds, but unlike the A-superfamily, these bonds are between cysteine residues 1-4 and 2-3.

As indicated above, conotoxin peptides bind to a range of different ion-channels in mammals, and accordingly they have several potential therapeutic applications, including pain relief and neuroprotection in humans. However, in general peptides have several difficulties associated with their use as drugs, including generally poor bioavailability, susceptibility to cleavage by proteases, and unwanted side effects.

One conotoxin, MVIIA (also known as SNX-111, Ziconitide and Prialt), recently received approval by the United States Food and Drug Administration for the treatment of intractable pain associated with cancer, AIDS and neuropathies. The route of administration is currently restricted to intrathecal infusion into the spinal cord because of some of the abovementioned difficulties.

The present invention is based on the finding that cyclisation of the peptide backbone of conotoxins to produce non-natural analogues results in new molecules which can retain the therapeutic activity of the non-cyclised peptide.

Accordingly in a first aspect the present invention provides a synthetically cyclised conotoxin peptide.

These cyclised conotoxin peptides/conotoxins have improved properties relative to their "linear" conotoxin counterparts. The improved properties may include the following:
1. Resistance to cleavage by proteases.
2. High chemical stability.
3. An additional "handle" on the molecule which does not interfere with the primary biological effect of the conotoxin, but provides a place for functionalising the molecule to improve biophysical properties or, in some cases, reduce side effects.
4. Improved bioavailability.

As used herein, unless the context requires otherwise, the term "linear" when used in connection with a conotoxin peptide means that the peptide is in a non-cyclised state, i.e. the N-terminus and C-terminus have not been linked (directly or with a linker) to form an amide cyclised backbone. Although the presence of one or more disulfide bonds in a conotoxin peptide will introduce a degree of circularity to the peptide, a peptide with such a disulfide bond is still to be regarded as "linear" if there is no cyclisation of the backbone of the peptide through linking of the N- and C-termini.

The linear conotoxin peptide may be any conotoxin peptide which is capable of being cyclised. It may be a naturally occurring conotoxin peptide, or a derivative thereof. Preferably the conotoxin peptide is one which, in its non-cyclised form, has an activity associated with the therapeutic treatment of mammals, such as humans. Since the cyclisation of the peptide has the potential to alter the activity of the peptide, or introduce new activities, it is possible that some cyclised conotoxin peptides may have improved therapeutic properties relative to "linear" conotoxins.

Examples of suitable linear naturally occurring conotoxins and derivatives thereof which may be cyclised according to the present invention include those described in Olivera, B. M. et al., 1991; Myers, R. A. et al., 1993; Hopkins, C. et al., 1995; Olivera, B. M. et al., 1990. Preferably the conotoxins are selected from the ω-class, which have characteristic three disulfide bonds forming a "cystine knot", although other classes of conotoxins may also be cyclised.

Examples of suitable naturally occurring co-conotoxin peptides include MVIIA, GVIA, SVIB, SVIA, TVIA, MVIIC, GVIIA and GVIIB.

The conotoxin peptides have a characteristic folding pattern which is based on the number of disulfide bonds, and the location on the peptide of the cysteine residues which participate in the disulfide bonding pattern. Where there are three disulfide bonds there is the potential for the peptide to form a cystine knot. A cystine knot occurs when a disulfide bond passes through a closed cyclic loop formed by two disulfide bonds and amino acids in the peptide chain. The cyclisation of a conotoxin having a cystine knot produces a particularly stable peptide structure. As well as being present in the class of omega-conotoxins (Nielsen, et al., 1996), the cystine knot exists in other classes including, $K^+$ channel blockers (eg conotoxin PVIIA; Scanlon et al., 1997) and Na channel blockers (eg conotoxin GS; Hill et al., 1997).

Preferred conotoxin peptides are those in which, in their folded form, have N- and C-termini which are located in close proximity. The proximity of termini is illustrated above for MVIIA and PVIIA. In conotoxin GS the N and C termini are further apart, but the C terminus contains a flexible tail which can readily alter conformation to approach the N terminus.

The cyclic conotoxin peptides according to the present invention will generally consist of a conotoxin peptide in which the N- and C-termini are linked via a linking moiety, although in some cases it may be possible to directly connect the N- and C-termini of a naturally occurring conotoxin peptide or derivative thereof without the need for a linking moiety. The linking moiety, if present, may be a peptide linker such that cyclisation produces an amide-cyclised peptide backbone. These peptides will have no free N- or C-termini.

Accordingly in this aspect of the present invention there is provided a cyclised conotoxin peptide comprising a linear conotoxin peptide and a peptide linker, wherein the N- and C-termini of the linear peptide are linked via the peptide linker to form an amide cyclised peptide backbone.

No examples of cyclic conotoxins have been previously described in the literature, but it is in principle possible to make molecules which have a cyclic backbone, part of which incorporates the natural sequence and disulfide bond connections of linear conotoxins.

Considerable variation in the peptide sequence of the linking moiety is possible. Since this linking region does not bind to or occlude the primary active site of the conotoxin it can be modified to alter physiochemical properties, and potentially reduce side effects of the conotoxins.

In linking the N- and C-termini of the conotoxin it may in some cases be necessary or desirable to remove one or more of the N- or C-termini residues. Such modification of the linear conotoxin sequence is within the scope of the present invention.

The linking moiety will necessarily be of sufficient length to span the distance between the N- and C-termini of the conotoxin peptide. In the case of peptide linkers the length will generally be in the order of 2 to 15 amino acids. In some cases longer or shorter peptide linkers may be required. In one embodiment the linker is composed of glycine and/or ananine residues in addition to any amino acid residues already present in the linear conotoxin.

Examples of other possible peptide linkers include:

| | |
|---|---|
| TRNGLPG | SEQ ID NO. 1; |
| TRNG | SEQ ID NO. 2; |
| TRGGLPV | SEQ ID NO. 3; and |
| TNG | SEQ ID NO. 4. |

In a particularly preferred embodiment of the invention the conotoxin peptide to be cyclised is a member of the A-superfamily having two disulfide bonds. For such conotoxin peptides it has been found that the distance between cysteine residues 1 and 4 is substantially conserved. For such conotoxin peptides, allowing for bond angles and distance, the linker length is preferably chosen such that the number of amino acids between cysteine residue 1 and 4 is between six and eight. Accordingly, for the α-conotoxin MII, the additional amino acid residues required for the linker would be between five and seven, allowing for the single amino acid already present at the N-terminus.

Accordingly to this aspect the invention provides a synthetically cyclised conotoxin peptide having an amide cyclised backbone such that the peptide has no free N- or C-terminus, said conotoxin peptide being a member of the A-superfamily and comprising four cysteine residues bonded in pairs to form two disulfide bonds, wherein the N-terminus of the corresponding linear/non-cyclised conotoxin peptide is linked to the C-terminus by a peptide linker such that between six and eight natural or unnatural amino acids span the distance between the first and the fourth cysteine residue.

Preferably the conotoxin peptide is an α- or ρ-conotoxin peptide, more preferably an α-conotoxin peptide.

Preferably the number of amino acids in the linker is selected such that there are seven amino acids between the first and the fourth cysteine residues. Depending on the sequence of the linear peptide, some or all of these residues may be derived from the linear sequence.

Accordingly if the conotoxin peptide has one amino acid at the N-terminus adjacent cysteine residue 1, the number of additional amino acids required for the linker would be six.

It has also been found that there is an optional linker length for χ-conotoxin peptides. Such a linker is chosen such that there are from four to six natural or unnatural amino acid residues between the first and fourth cysteine residues.

According to this aspect the invention provides a synthetically cyclised conotoxin peptide having an amide cyclised backbone such that the peptide has no free N- or C-terminus, said conotoxin peptide being a chi conotoxin peptide and comprising four cysteine residues bonded in pairs to form two disulfide bonds, wherein the N-terminus of the corresponding linear/non-cyclised conotoxin peptide is linked to the C-terminus by a peptide linker such that between four and six natural or unnatural amino acids span the distance between the first and the fourth cysteine residues.

Preferably the number of amino acids in the linker is selected such that there are five amino acids between the first and fourth cysteine residues. Accordingly if a chi peptide has three amino acids at the N-terminus adjacent to cysteine residue 1, such as for MrIA, the number of additional amino acids would be two.

Of course it would also be possible to substitute one or more of the N-terminal residues with another residue which would form part of the linker.

It is possible, according to the present invention, to modify or potentiate the activity of a conotoxin peptide by selection of a particular size and/or type of peptide linker. Small changes in the conformation of the conotoxin caused by the introduction of a linking group can alter the binding affinities of the peptides for their particular binding sites. Conversely, where the activity is to be as close to the activity of the parent conotoxin peptide as possible, a linker will be selected which minimises any change in conformation.

There are several ways in which linear conotoxins may be cyclised. These include the following:

1. Cyclisation of the Reduced Peptide Followed by Oxidation to Form the Required Disulfide Bonds In this approach an extended linear peptide is first synthesised "on resin" using solid phase peptide synthesis methods. This extended linear peptide comprises the native sequence starting at a cysteine residue at, or closest to, the N-terminus and a C-terminal extension which comprises the new linking moiety. The solid phase synthesis actually starts in the reverse order—ie at the C-terminus of the extended linear peptide. Following cleavage from the resin, the extended conotoxin is cyclised to a thioester intermediate which subsequently rearranges to an amide-cyclised peptide. This reduced peptide is then oxidised to form the disulfide bonds. A schematic diagram of the reaction involved in the cyclisation is shown in FIG. 2. The linear peptide is cleaved from the resin with the linker to the resin (R) still attached. R corresponds to the linker between the peptide and the resin and is different from the linking moiety used in the cyclisation. The first reaction involves the formation of a thioester between the thiol of the N-terminal cysteine and the carboxy terminus. This then undergoes an S, N acyl migration to form the cyclic peptide with a native peptide bond.

2. Oxidation of the Reduced Linear Peptide, Followed by Cyclisation

In this approach an extended peptide is assembled using solid phase peptide synthesis. The extended linear peptide comprises the native conotoxin sequence with extra residues added at the N- and/or C-termini. The (new) N and C termini should preferably be glycine residues. The peptide is folded, and in the case of the conotoxin-like peptides, the termini of the folded molecule are generally close together in space. This facilitates the cyclisation of the peptide in solution using standard chemistry. Complications may occur when large numbers of lysine, glutamic acid or aspartic acid residues are present in the sequence and method 1 is then preferable.

3. Ligation of a Linker onto an Existing Conotoxin, Followed by Cyclisation

In this method the starting material is a mature conotoxin. A peptide linker is synthesised and ligated with the conotoxin using published procedures for the ligation of peptides. The extended peptide is then cyclised and oxidised.

Accordingly in a further aspect of the invention there is provided a process for preparing a cyclic conotoxin comprising:

A
(i) synthesising an extended linear conotoxin peptide on a solid phase support, said extended linear conotoxin peptide comprising a linear conotoxin peptide having a linker moiety attached to at least one end thereof,
(ii) cleaving said extended linear peptide from the support
(iii) cyclising said extended linear conotoxin peptide, and
(iv) oxidising said cyclised peptide to form disulfide bonds, or B
(i) synthesising an extended linear conotoxin peptide on a solid phase support, said extended linear conotoxin peptide comprising a linear conotoxin peptide having a linker moiety attached to at least one end thereof,
(ii) cleaving said extended linear peptide from the solid support (iii) subjecting said extended peptide to conditions such that the peptide folds and forms the required disulfide bonds, and
(iv) cyclising the folded peptide, or C
(i) reacting a conotoxin peptide with a linker moiety to form an extended linear conotoxin peptide having said linker moiety attached to one end thereof, and
(ii) cyclising said extended peptide and oxidising to form disulfide bonds, if required.

In the process described above the steps can be performed in any order, provided the product is a cyclic conotoxin having the required disulfide bonds. For example, in process A the cleavage and cyclisation steps may be performed simultaneously or in either order. Similarly in process B the cyclisation and folding steps could be performed simultaneously, or in either order.

It is also possible to form the disulfide bonds selectively using protecting groups on the cysteine residues. Selective protection of the cysteine residues in this way allows the production of a particular disulfide bond pattern. Examples of groups capable of protecting cysteine residues include acetamidomethyl (Acm), 4-methylbenzyl (MeBzl) and 4-methoxybenzyl (Mob).

Also, in view of the cyclic nature of the final products, synthetic procedures may involve cyclic permutation of the above procedures. For example, the designs of the extended linear peptide for α-conotoxins could commence by adding a linker to the C-terminal residue of the α-conotoxin, cyclically permuting the N-terminal residue(s) to the C-terminal, to provide an N-terminal cysteine, and cyclising as described.

Some examples of linear conotoxins which are currently known and to which the cyclisation approach can be applied are listed in Table 1.

TABLE 1

Amino acid sequences of selected known conotoxins.

| Conotoxin | Sequence |
|---|---|
| Omega conotoxins | |
| MVIIA | CKGKGAKCSRLMYDCCTGSCRS--GKC SEQ ID NO. 18 |
| MVIIC | CKGKGAOCRKTMYDCCSGSCGRR-GKC SEQ ID NO. 19 |
| GVIA | CKSOGSSCSOTSYNCCR-SCNOYTKRCY SEQ ID NO. 20 |
| SVIA | CRSSGSOCGVTSI-CCGR-CYR--GKCT SEQ ID NO. 21 |
| SVIB | CKLKGQSCRKTSYDCCSGSCGRS-GKC SEQ ID NO. 22 |
| GVIIA | CKSOGTOCSRGMRDCCTS-CLLYSNKCRRY SEQ ID NO. 23 |
| GVIIB | CKSOGTOCSRGMRDCCTS-CLSYSNKCRRY SEQ ID NO. 24 |
| TVIA | CLSOGSSCSOTSYNCCRS-CNOYSRKCR SEQ ID NO. 25 |
| Kappa conotoxin | |
| PVIIA | CRIONQKCFQHLDDCCSRKCNRFNKCV SEQ ID NO. 26 |

TABLE 1-continued

Amino acid sequences of selected known conotoxins.

| Conotoxin | Sequence | |
|---|---|---|
| Alpha conotoxins | | |
| GI | ECCNPA-CGRHYS--C | SEQ ID NO. 27 |
| IMI | GCCSDPRCAWR----C | SEQ ID NO. 28 |
| PNIA | GCCSLPPCAANNPDYC | SEQ ID NO. 29 |
| PNIB | GCCSLPPCALSNPDYC | SEQ ID NO. 30 |
| SII | GCCCNPACGPNYG--CGTSCS | SEQ ID NO. 31 |
| MII | GCCSNPBCHLEHSNLC | SEQ ID NO. 32 |
| Mu conotoxins | | |
| GIIIA | -RDCCTOOKKCKDRQCKOQRCCA | SEQ ID NO. 33 |
| GIIIB | -RDCCTOORKCKDRRCKOMKCCA | SEQ ID NO. 34 |
| GIIIC | -RDCCTOOKKCKDRRCKOLKCCA | SEQ ID NO. 35 |
| PIIIA | ZRLCCGFOKSCRSRQCKOHRCC | SEQ ID NO. 36 |
| MuO conotoxin | | |
| GS | ACSGRGSRCPPQCCMGLRCGRGNPQKCIGAHEDV | SEQ ID NO. 37 |
| Chi conotoxins | | |
| MrIA | NGVCCGYKLCHOC | SEQ ID NO. 15 |

It should be noted that all of the omega, kappa and MuO conotoxins in Table 1 are members of the O-superfamily, while all of the alpha conotoxins, with the exception of SII, are members of the A-superfamily.

The term "derivative" as used herein in connection with naturally occurring conotoxin peptides, such as MVIIA, refers to a peptide which differs from the naturally occurring peptides by one or more amino acid deletions, additions, substitutions, or side-chain modifications.

Substitutions encompass amino acid alterations in which an amino acid is replaced with a different naturally-occurring or a non-conventional amino acid residue. Such substitutions may be classified as "conservative", in which case an amino acid residue contained in a polypeptide is replaced with another naturally-occurring amino acid of similar character either in relation to polarity, side chain functionality, or size, for example Ser↔Thr↔Pro↔Hyp↔Gly↔Ala, Val↔Ile↔Leu, His↔Lys↔Arg, Asn↔Gln↔Asp↔Glu or Phe↔Trp↔Tyr. It is to be understood that some non-conventional amino acids may also be suitable replacements for the naturally occurring amino acids. For example ornithine, homoarginine and dimethyllysine are related to His, Arg and Lys.

Substitutions encompassed by the present invention may also be "non-conservative", in which an amino acid residue which is present in a polypeptide is substituted with an amino acid having different properties, such as a naturally-occurring amino acid from a different group (eg. substituting a charged or hydrophobic amino acid with alanine), or alternatively, in which a naturally-occurring amino acid is substituted with a non-conventional amino acid.

Amino acid substitutions are typically of single residues, but may be of multiple residues, either clustered or dispersed.

Preferably, amino acid substitutions are conservative.

Additions encompass the addition of one or more naturally occurring or non-conventional amino acid residues. Deletion encompasses the deletion of one or more amino acid residues.

As stated above the present invention includes peptides in which one or more of the amino acids has undergone sidechain modifications. Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of mixed disulfides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues must riot affect the ability of the peptide to form the necessary disulfide bonds. It is also possible to replace the sulphydryl groups of cysteine with selenium equivalents such that the peptide forms a diselenium bond in place of one or more of the disulfide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Proline residues may be modified by, for example, hydroxylation in the 4-position.

A list of some amino acids having modified side chains and other unnatural amino acids is shown in Table 2.

TABLE 2

| Non-conventional amino acid | Code |
|---|---|
| L-α-aminobutyric acid | Abu |
| α-amino-α-methylbutyrate | Mgabu |
| aminocyclopropanecarboxylate | Cpro |
| aminoisobutyric acid | Aib |
| aminonorbornylcarboxylate | Norb |

TABLE 2-continued

| Non-conventional amino acid | Code |
|---|---|
| cyclohexylalanine | Chexa |
| cyclopentylalanine | Cpen |
| D-alanine | DAla |
| D-arginine | DArg |
| D-asparagine | DAsn |
| D-aspartic acid | DAsp |
| D-cysteine | DCys |
| D-glutamine | DGln |
| D-glutamic acid | DGlu |
| D-histidine | DHis |
| D-isoleucine | DIle |
| D-leucine | DLeu |
| D-lysine | DLys |
| D-methionine | DMet |
| D-ornithine | DOrn |
| D-phenylalanine | DPhe |
| D-proline | DPro |
| D-serine | DSer |
| D-threonine | DThr |
| D-tryptophan | DTrp |
| D-tyrosine | DTyr |
| D-valine | DVal |
| D-α-methylalanine | DMala |
| D-α-methylarginine | DMarg |
| D-α-methylasparagine | DMasn |
| D-α-methylaspartate | DMasp |
| D-α-methylcysteine | DMcys |
| D-α-methylglutamine | DMgln |
| D-α-methylhistidine | DMhis |
| D-α-methylisoleucine | DMile |
| D-α-methylleucine | DMleu |
| D-α-methyllysine | DMlys |
| D-α-methylmethionine | DMmet |
| D-α-methylornithine | DMorn |
| D-α-methylphenylalanine | DMphe |
| D-α-methylproline | DMpro |
| D-α-methylserine | DMser |
| D-α-methylthreonine | DMthr |
| D-α-methyltryptophan | DMtrp |
| D-α-methyltyrosine | DMty |
| D-α-methylvaline | DMval |
| D-N-methylalanine | DNmala |
| D-N-methylarginine | DNmarg |
| D-N-methylasparagine | DNmasn |
| D-N-methylaspartate | DNmasp |
| D-N-methylcysteine | DNmcys |
| D-N-methylglutamine | DNmgln |
| γ-carboxyglutamate | Gla |
| 4-hydroxyproline | Hyp |
| 5-hydroxylysine | Hlys |
| 2-aminobenzoyl (anthraniloyl) | Abz |
| Cyclohexylalanine | Cha |
| Phenylglycine | Phg |
| 4-phenyl-phenylalanine | Bib |
| L-Citrulline | Cit |
| L-1,2,3,4-tetrahydroisoquinoline-3-carboxylic acid | Tic |
| L-Pipecolic acid (homoproline) | Pip |
| L-homoleucine | Hle |
| L-Lysine (dimethyl) | DMK |
| L-Naphthylalanine | Nal |
| L-dimethyldopa or L-dimethoxyphenylalanine | DMD |
| L-thiazolidine-4-carboxylic acid | THZ |
| L-homotyrosine | hTyr |
| L-3-pyridylalanine | PYA |
| L-2-furylalanine | FLA |
| L-histidine(benzyloxymethyl) | HBO |
| L-histidine(3-methyl) | HME |
| D-N-methylglutamate | DNmglu |
| D-N-methylhistidine | DNmhis |
| D-N-methylisoleucine | Dnmile |
| D-N-methylleucine | DNmleu |
| D-N-methyllysine | DNmlys |
| N-methylcyclohexylalanine | Nmchexa |
| D-N-methylornithine | DNmorn |
| N-methylglycine | Nala |
| N-methylaminoisobutyrate | Nmaib |
| N-(1-methylpropyl)glycine | Nile |

| Non-conventional amino acid | Code |
|---|---|
| N-(2-methylpropyl)glycine | Nleu |
| D-N-methyltryptophan | DNmtrp |
| D-N-methyltyrosine | DNmtyr |
| D-N-methylvaline | DNmval |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| N-cycloheptylglycine | Nchep |
| N-(3-guanidinopropyl)glycine | Narg |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethylglycine | Nnbhm |
| 1-carboxy-1-(2,2-diphenylethylamino)cyclopropane | Nmbc |
| L-N-methylalanine | Nmala |
| L-N-methylarginine | Nmarg |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcyclopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(hydroxyethyl)glycine | Nser |
| N-(imidazolylethyl))glycine | Nhis |
| N-(3-indolylyethyl)glycine | Nhtrp |
| N-methyl-γ-aminobutyrate | Nmgabu |

TABLE 2-continued

| Non-conventional amino acid | Code |
| --- | --- |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalani | Nmhphe |
| N-(N-(3,3-diphenylpropyl)carbamylmethylglycine | Nnbhe |
| O-methyl-L-serine | Omser |
| O-methyl-L-homoserine | Omhser |
| O-methyl-L-tyrosine | MeY |
| γ-aminobutyric acid | Gabu |
| O-methyl-L-homotyrosine | Omhtyr |
| L-β-homolysine | BHK |
| L-ornithine | Orn |
| N-cyclohexylglycine | Nchex |
| D-N-methylserine | $_D$Nmser |

These types of modifications may be important to stabilise the peptide if administered to an individual or for use as a diagnostic reagent.

Other derivatives contemplated by the present invention include a range of glycosylation variants from a completely unglycosylated molecule to a modified glycosylated molecule. Altered glycosylation patterns may result from expression of recombinant molecules in different host cells.

Preferably the cyclised conotoxin peptides will retain the Cys residues and characteristic disulfide bonding pattern. Derivatives may include additional Cys residues provided they are protected during formation of the disulfide bonds.

Preferably the conotoxin peptides according to the invention have 12 to 40 amino acids, more preferably 15 to 30.

Naturally occurring conotoxins are widely used as neuropharmacological probes. They bind very tightly and highly selectively to ion channel receptors. In these applications they are incubated with a relevant tissue preparation and their binding, or biological effects are measured. Their actions will be reduced or destroyed if they are metabolized by endogenous enzymes. Optimum performance of pharmacological probes thus requires resistance to enzymatic or chemical breakdown. Since the cyclised conotoxin peptides possess the desirable properties described above they may be better pharmacological probes than naturally occurring "linear" conotoxin peptides in some cases.

Still another aspect of the present invention is directed to antibodies to the cyclic peptides according to the invention. Such antibodies may be monoclonal or polyclonal and may be selected from naturally occurring antibodies to the peptides or may be specifically raised to the peptides using standard techniques. In the case of the latter, the peptides may first need to be associated with a carrier molecule. The antibodies of the present invention are particularly useful as therapeutic or diagnostic agents.

In this regard, specific antibodies can be used to screen for the peptides according to the invention. Techniques for such assays are well known in the art and include, for example, sandwich assays and ELISA. Knowledge of peptide levels may be important for monitoring certain therapeutic protocols.

The cyclised conotoxin peptides according to the present invention are useful as therapeutic agents.

Accordingly the present invention provides a method for the treatment or prophylaxis of conditions or diseases in mammals, preferably humans, including the step of administering a cyclised conotoxin peptide.

In particular omega-conotoxins which block N-type calcium channels may be useful in the treatment of neurological disorders such as acute and chronic pain, stroke, traumatic brain injury, migraine, epilepsy, Parkinson's disease, Alzheimer's disease, multiple schlerosis, and depression. The α-conotoxins bind to nicotinic acetylcholine receptors (nAChRs). Such receptors have been implicated in the pathophysiology of several neuropsychiatric disorders including schizophrenia, Alzheimer's disease, Parkinson's disease and Tourette's syndrome and thus the α-conotoxins have potential therapeutic indications for these diseases. The μ-conotoxins target sodium channels. Those μ-conotoxins that interact with neuronal channels (eg PIIIA) have potential therapeutical applications in the treatment of chronic and neuropathic pain. Cyclised χ-conotoxins also have the potential to treat pain.

Assays useful for assessing compounds with the above mentioned activities may be in vitro or in vivo and are known to those skilled in the art. For example, assays useful for assessing activity at N-type calcium channels include those described or referenced in WO91/07980, WO93/13128, U.S. Pat. No. 5,824,645, WO97/04797, Drugs of the Future (1994 and 1998), Drug Data Report (1993), or Heading (1999). The cyclic peptides according to the invention, or labelled derivatives thereof, may also be useful in such assays.

Preferably the mammal is in need of such treatment although the peptide may be administered in a prophylactic sense.

The invention also provides a composition comprising a cyclised conotoxin peptide, and a pharmaceutically acceptable carrier or diluent.

Preferably the composition is in the form of a pharmaceutical composition.

There is also provided the use of a cyclised conotoxin peptide in the manufacture of a medicament for the treatment or prophylaxis of diseases or conditions of mammals, preferably of humans.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the peptide actives care should be taken to ensure that the activity of the peptide is not destroyed in the process and that the peptide is able to reach its site of action without being destroyed. In some circumstances it may be necessary to protect the peptide by means known in the art, such as, for example, micro encapsulation. Similarly the route of administration chosen should be such that the peptide reaches its site of action. In view of the improved stability of the cyclised peptides relative to their "linear" counterparts a wider range of formulation types and routes of administration is available. Known conotoxins can generally only be administered successfully intrathecally which means that the patient must be hospitalised. Administration of the cyclised peptides according to the present invention is not subject to the same restriction.

The pharmaceutical forms suitable for injectable use include sterile injectable solutions or dispersions, and sterile powders for the extemporaneous preparation of sterile injectable solutions. They should be stable under the conditions of manufacture and storage and may be preserved against the contaminating action of microorganisms such as bacteria or fungi. The solvent or dispersion medium for the injectable solution or dispersion may contain any of the conventional solvent or carrier systems for peptide actives, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolality, for example, sugars or sodium chloride. Preferably, the formulation for injection will be isotonic with blood. Prolonged absorption of the injectable compositions can be brought about by the use in the compositions of agents delaying absorption, for example, aluminium monostearate and gelatin. Pharmaceutical forms suitable for injectable use may be delivered by any appropriate route including intravenous, intramuscular, intracerebral, intrathecal injection or infusion.

Sterile injectable solutions are prepared by incorporating the active compounds in the required amount in the appropriate solvent with various of the other ingredients enumerated above, as required, followed by. filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredient is suitably protected it may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations preferably contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to any other forms suitable for administration, for example topical application such as creams, lotions and gels, or compositions suitable for inhalation or intranasal delivery, for example solutions or dry powders.

Parenteral dosage forms are preferred, including those suitable for intravenous, intrathecal, or intracerebral delivery.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form. A unit dosage form can, for example, contain the principal active compound in amounts ranging from 0.25 µg to about 2000 mg. Expressed in proportions, the active compound is generally present in from about 0.25 µg to about 2000 mg/ml of carrier. In the case of compositions containing supplementary active ingredients, the dosages are determined by reference to the usual dose and manner of administration of the said ingredients.

The invention will now be described with reference to the accompanying examples and figures which describe the production of some cyclised conotoxin peptides and their biological activity and illustrate the structures of some linear conotoxin peptides which may be subjected to cyclisation. However, it is to be understood that the particularity of the following description is not to supersede the generality of the preceding description of the invention.

Referring to the figures:

FIG. 1 is a representation of the three-dimensional structures of the conotoxins PVIIA; MVIIA and GS. The structures were determined by NMR spectroscopy. The backbone atoms are displayed as lines and the disulfide bonds are highlighted as balls and sticks. All three conotoxins, although from different classes and hence having different activities, have similar structures which contain a cystine knot motif.

FIG. 2 is a scheme for peptide cyclisation via a C-terminal thioester. The free sulfur of an N-terminal cysteine interacts with the C-terminal thioester to form an intermediate which undergoes an S, N, acyl migration to form a cyclised peptide with a native peptide bond.

FIG. 3 is a representation of the three-dimensional structures of the conotoxins PVIIA, MVIIA, SVIB, GI and ImI. The structures were determined by NMR spectroscopy. The backbone atoms are shown as lines and the N- and C-termini are connected by a dotted line which has the intervening distance shown above. The α-conotoxins, GI and ImI, have slightly closer termini than the conotoxins shown in the top of the figure, which suggests cyclisation would be more feasible for this class of conotoxins and may even occur more readily than that shown for MVIIA.

FIG. 4 is a representation of the three-dimensional structures of the conotoxins MII, cMII-6 and cMII-7, and includes an overlay of these structures. The disulfide bonds are represented by ball and sticks. The structures were determined by NMR spectroscopy.

Figure 8:
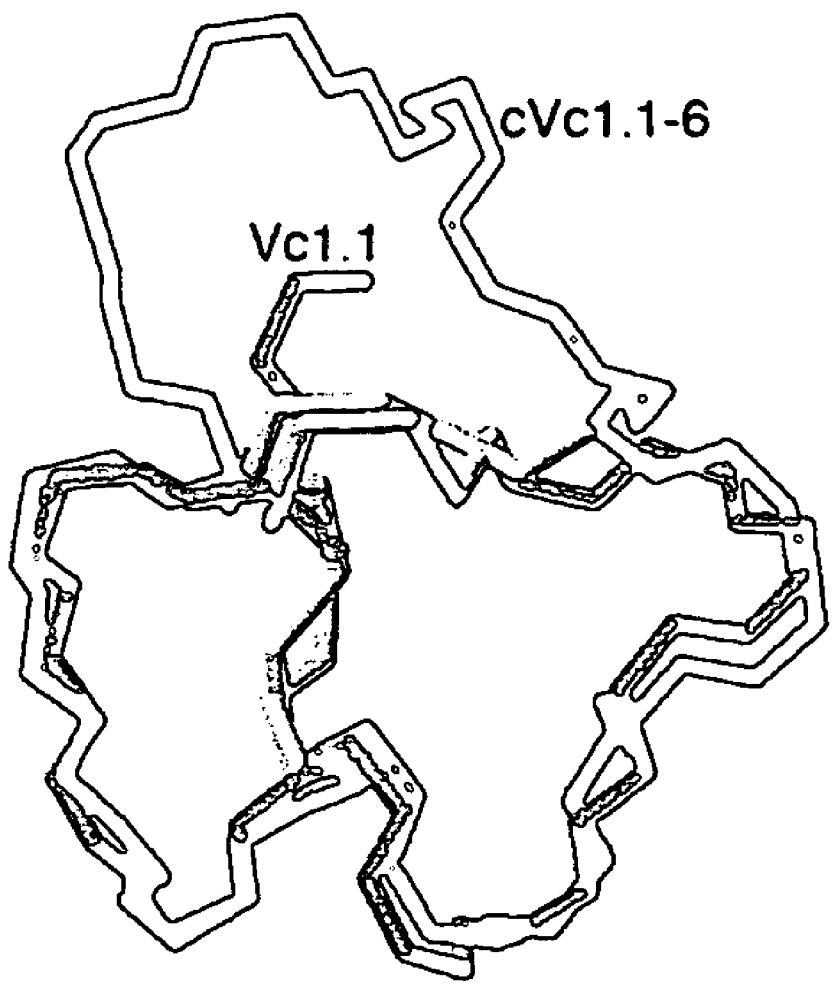

FIG. 8 is a representation of the three dimensional structure of both Vc1.1 and cyclic Vc1.1-6. The structures were determined using NMR spectroscopy. The structures indicate the native conformation of Vc1.1-6 is retained in cyclic Vc1.1-6.

Figure 9:
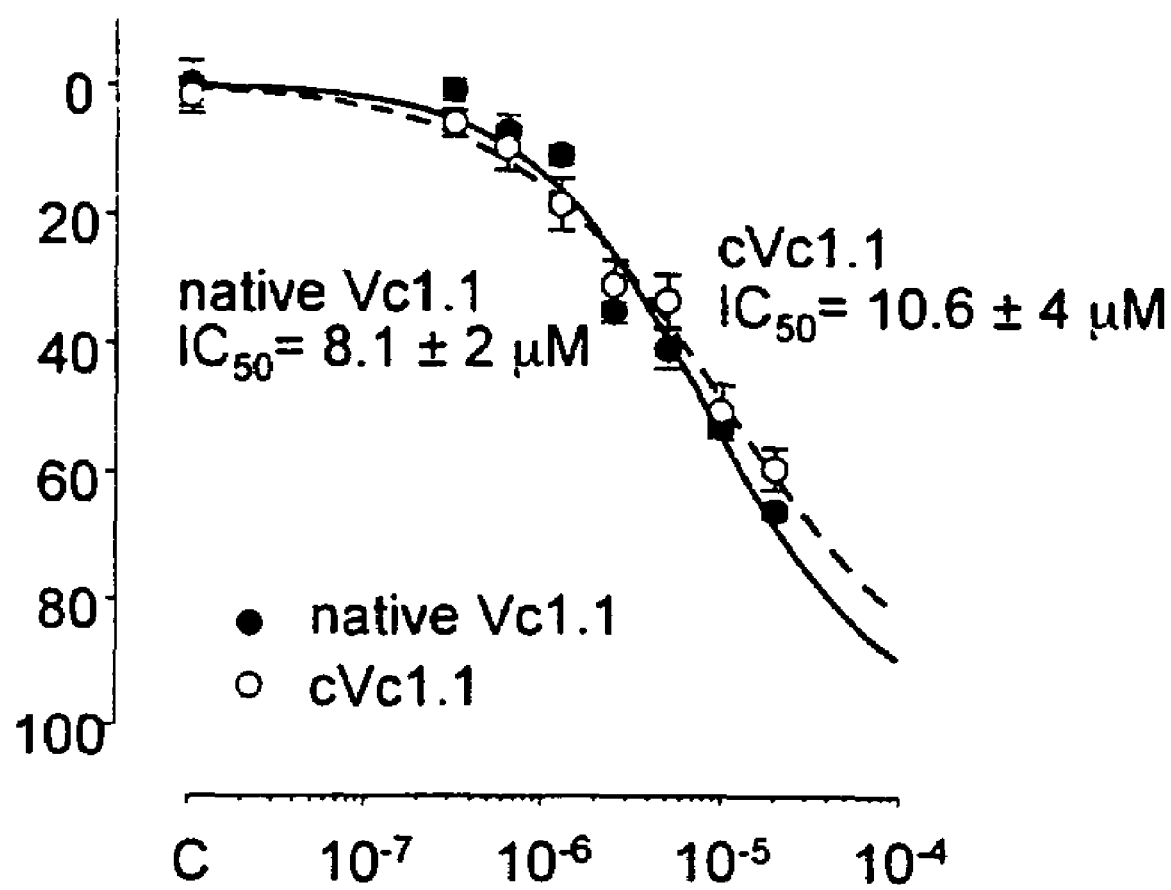

FIG. 9 is a graph depicting the relative biological activity of cyclic Vc1.1-6 and Vc1.1, as assessed by measuring catchecholamine release from bovine adrenal chromaffin cells. Chromaffin cells were incubated with indicated amount of peptides for 20 min and then stimulated with 10 μM nicotine for 20 min in the continuing presence of inhibitors. Aliquots were removed and assayed fluorimetrically for catecholamine secretion (n=6 experiments) as previously described (Meunier et al., 2002).

Figure 10:
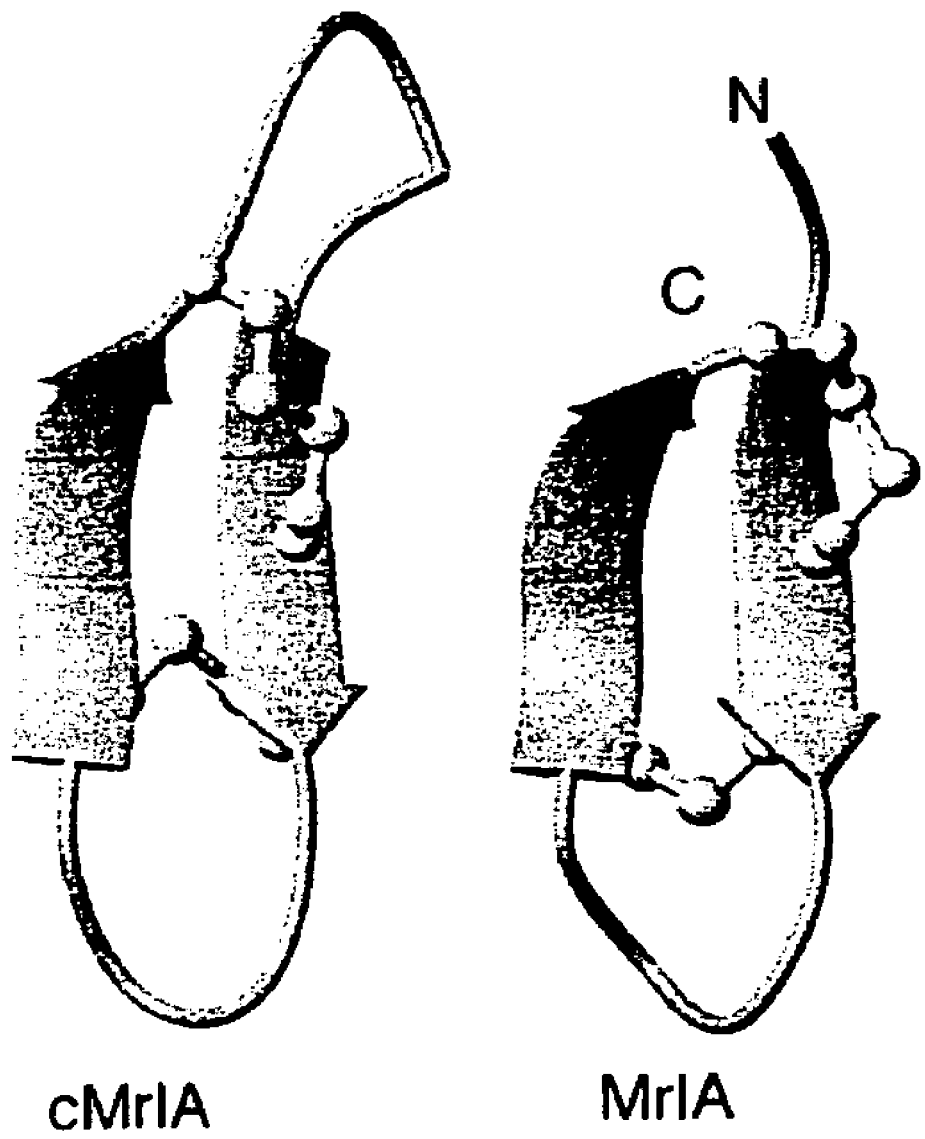

FIG. 10 is a representation of the 3D structure of cyclic MrIA and linear MrIA, shown in ribbon format, with the arrows representing β-strands and the disulfide bonds shown in ball and stick format. The N- and C-termini of MrIA are labelled. The structures were determined using NMR spectroscopy. The structure indicates the native conformation of MrIA is retained in cyclic MrIA.

Figure 11:
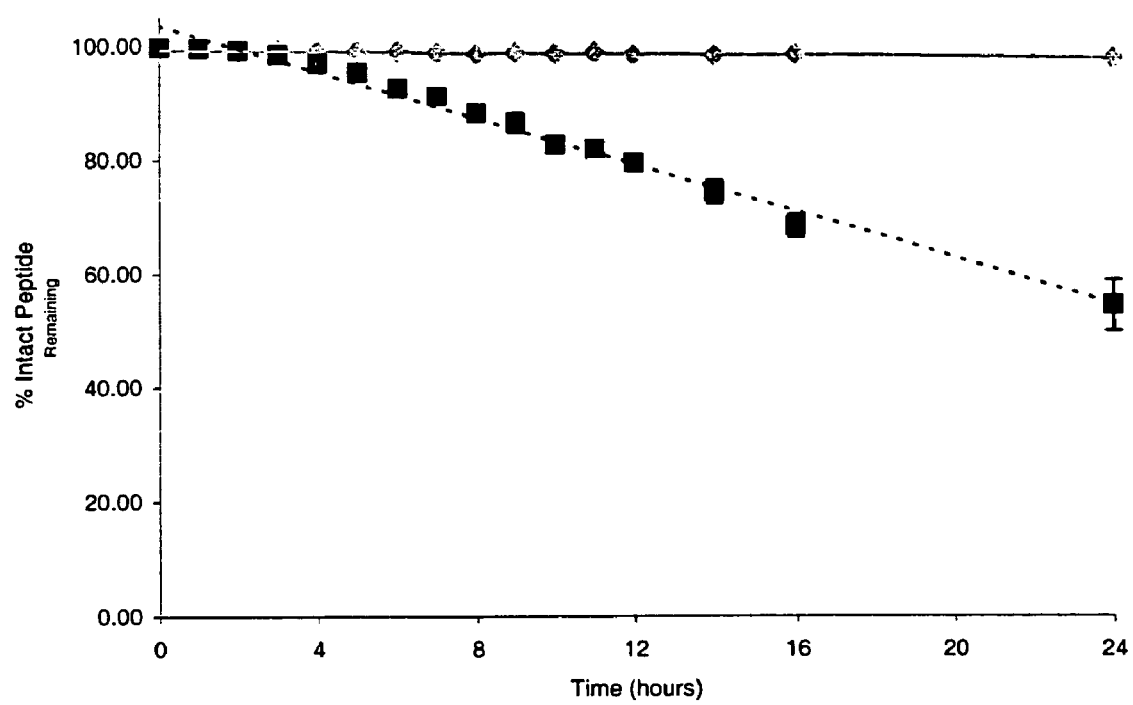

FIG. 11 is a graph depicting the relative stability of cyclic MrIA and MrIA against cleavage by trypsin performed with the substrate:enzyme ratio of 20:1. Cyclic MrIA is shown as grey diamonds and MrIA as black squares.

Figure 12:
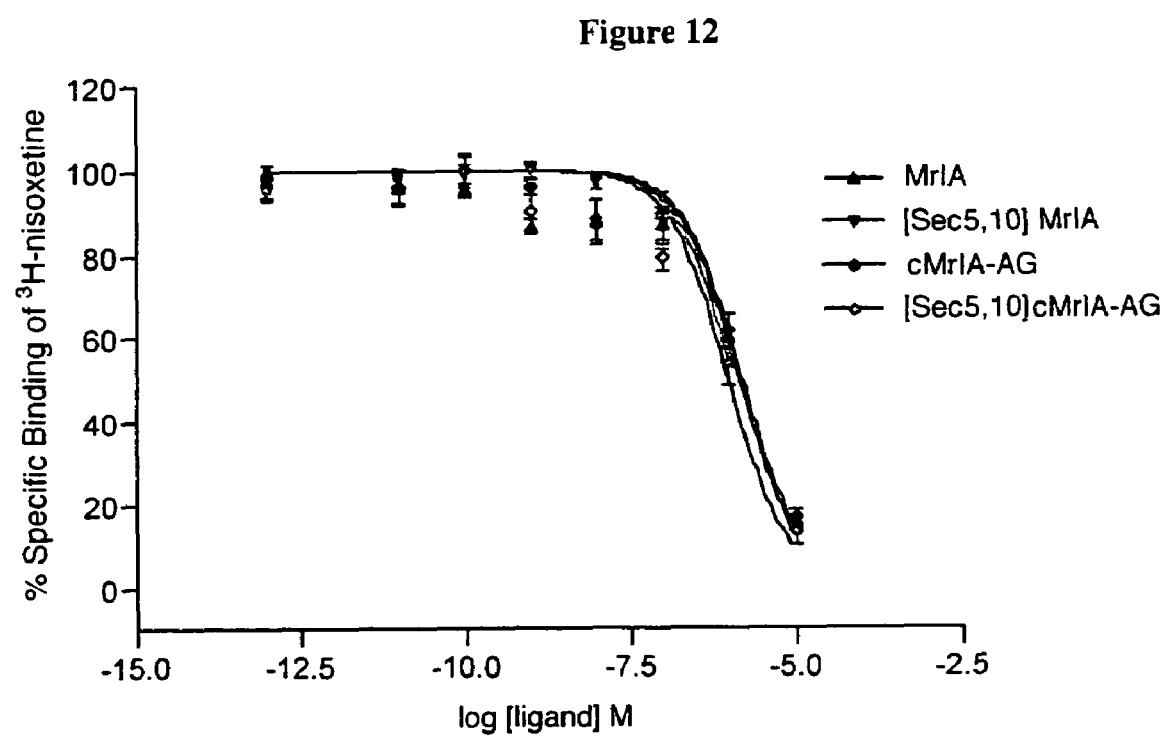

FIG. 12 shows specific binding of MrIA and analogues against $^3$H-nisoxetine in Cos7-hNET membrane. Data has been normalised to give a % specific binding.

EXAMPLES

Example 1

A cyclic analogue of MVIIA (cyclo-MVIIA 1) has been synthesised with the sequence:

CKGKGAKCSRLMYDCCTGSCRSGKCTRNGLPG

SEQ ID NO.5

The residues in bold represent the sequence of MVIIA. Those not in bold are the linking moiety (TRNGLPG) (SEQ ID NO. 1). A thioester method has been used in the synthesis of this peptide which was performed on a Gly PAM resin. A —SCH$_2$—CH$_2$CO— linker was attached to the Gly-PAM resin by treating the resin with bromopropanoic acid for 30 minutes, washing with DMF and then treating the resin with 10% thioacetic acid, 10% DIEA in DMF for 2×20 minutes. The resin was again washed with DMF and treated with 10% β-mercaptoethanol, 10% DIEA in DMF for 2×20 minutes. After a final wash with DMF, the first residue, Boc-glycine, was coupled to the resin using HBTU and DIEA. The remainder of the peptide was assembled by manual synthesis using HBTU with in situ neutralisation (Schnölzer, M. et al., 1992).

The linker is not stable under basic conditions, thus the formyl group was not removed from the tryptophan with ethanolamine prior to HF cleavage. Cresol (800 μL) and thiocresol (200 μL) were used as scavengers during the HF cleavage which was carried out for 2 hours at −2 to 0° C. The crude, reduced peptide was purified using preparative reverse-phase HPLC on a Vydac C18 column. Gradients of 0.1% aqueous TFA and 90% acetonitrile/0.09% TFA were employed with a flow rate of 8 mL/min and the eluant monitored at 230 nm. The reduced peptide was cyclised in 0.1M sodium phosphate (pH 7.4), with a 6 fold excess of TCEP at room temperature for 30 minutes. All linear material was cyclised within this time as judged by analytical reverse phase HPLC and mass spectrometry. Mass analysis was performed on a Sciex (Thornhill, Ontario) triple quadrupole mass spectrometer using electrospray sample ionization. Cyclo-MVIIA 1 was oxidized at a concentration of 0.5 mg/ml in 2M (NH$_4$)$_2$SO$_4$, 0.1 M NH$_4$OAc (pH 8) and 1 mM reduced glutathione at 4° C. for 24 hours. The product was purified using reverse phase preparative HPLC.

Example 2

A slightly smaller cyclic analogue of MVIIA (cyclo-MVIIA 2) has been synthesised with the sequence:

CKGKGAKCSRLMYDCCTGSCRSGKCTRNG
|_____|

SEQ ID NO.6

Once again the bold residues correspond to the sequence of MVIIA, (all except TRNG) (SEQ ID NO. 2). This peptide was synthesised using the procedures outlined in Example 1. Following cyclisation, cyclo-MVIIA 2 was oxidised at a concentration of 0.5 mg/mL in 2 M $(NH_4)_2SO_4$, 0.1M $NH_4OAc$ (pH 8) and 1 mM reduced glutathione at 4° C. for 24 hours. Three major components were present in the oxidation and were all purified using a semi-preparative C18 column (3 mL/min) with monitoring at 230 nm. The three components represent cyclic fully disulfide bonded forms of cyclo-MVIIA 2.

Example 3 a) Antagonists specific to N-type voltage-sensitive calcium channels are being used as leads in drug development. Examples of these are ω-conotoxins GVIA and MVIIA. An assay has previously been established to determine the ability of a compound to displace $^{125}$I-GVIA from receptors in rat membrane. Rat membrane was prepared according to the procedure of Wagner et al. 1988. Rats were sacrificed by cervical dislocation and their brains removed and immediately frozen in liquid nitrogen. Frozen brains were stored at −78° C. until required. Three brains (wet weight, 6.25 g) were thawed (50 mM HEPES, pH 7.4) and homogenised with ultraturrex (IKA, 170 Watt) in 125 mls 50 mM HEPES pH 7.4. Homogenised brain was centrifuged at 16000 rpm (35000 g) for 20 min at 4° C. and the supernatant discarded. The pellet was resuspended by further homogenisation in 50 mM HEPES, pH 7.4, 10 mM EDTA and incubated at 4° C. for 30 min. Centrifugation was repeated as above and the supernatant discarded. The pellet was resuspended in 125 ml 50 mM HEPES, pH 7.4 (1:20 dilution) and stored at −78° C.

$^{125}$I-[Tyr22]GVIA was prepared according to the procedure of Cruz and Olivera (1986) and isolated by reverse-phase HPLC on an analytical Vydac C18 column. The column was equilibrated in buffer A ($H_2O$, 0.1% TFA) followed by a linear gradient to 67% buffer B (90% acetonitrile, 10% $H_2O$ and 0.09% TFA) in 100 min. Peaks were detected at 214 nm and the flow rate was 1 ml/min. The radiolabeled peaks were counted using a gamma counter and stored at 4° C.

Assays were performed in 12×75 mm borasilicate culture tubes at room temperature and incubated for 1 hr. Each tube contained 100 μl each of test solution, iodinated ligand (7 fmol) and rat membrane (16 μg) added in this order. The assay buffer contained 20 mM HEPES pH 7.2, 75 mM NaCl, 0.1 mM EDTA, 0.1 mM EGTA, 0.1% BSA and protease inhibitors, 2 mM leupeptin and 0.5 U aprotinin. The nonspecific binding was determined in the presence of 17 nM GVIA. Assays were terminated by vacuum filtration on a Millipore manifold filtration system using glass fibre filters (Whatman GFB) presoaked in 0.6% polyethylenimine. Each tube was washed 3 times with 3 ml ice-cold wash buffer (20 mM HEPES pH 7.2, 125 mM NaCl and 0.1% BSA). Filters were counted on a gamma counter. Graphpad Prism was used to generate binding curves and calculate $EC_{50}$ values. The $EC_{50}$ values are a measure of the ability of a compound to displace $^{125}$I-GVIA; the $EC_{50}$ for MVIIA is $4.4×10^{-11}$ M. Fractions isolated from oxidation of the cysteine residues in cyclic, reduced cyclo-MVIIA 1 were tested in this assay. As expected, not all disulfide isomers had the same level of activity. The most active isomer exhibited an EC50 of 8.5×10−8 M. The three oxidized, cyclic forms of cyclo-MVIIA 2 were also tested in this assay and the most active isomer exhibited an EC50 of 5×10−10 M. As expected, not all disulfide isomers had the same level of activity.

b) To test the specificity of the cyclic conotoxin derivatives for the N-type Ca channel relative to P/Q type channels additional binding studies were done using $^{125}$I-MVIIC as the displaced ligand. This binds selectively to P/Q type Ca channels.

The assay was carried out as described in Example 3a, except that $^{125}$I-MVIIC (selective for P/Q-type) channels was used as the displaced ligand rather than $^{125}$I-GVIIA (selective for N-type channels). The $^{125}$I-MVIIC was prepared and purified as described in Nielsen et al, 1999.

The most active form of cyclo-MVIIA 2 did not show any ability to displace $^{125}$I-MVIIC when administered at concentrations up to 630 nM. When combined with the data described above for displacement of $^{125}$I-GVIIA from N-type channels, this demonstrates selectivity for the N-type channel over the P/Q-type channel.

Example 4

Figure 1:
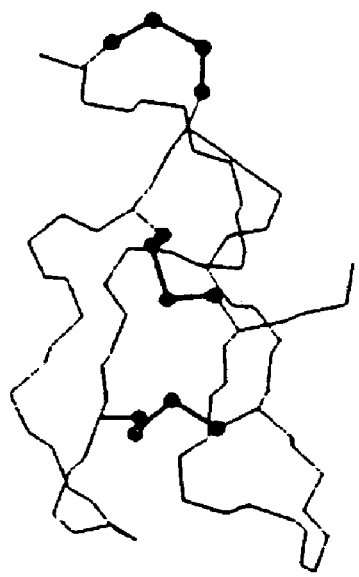
Figure 1:
Figure 1:
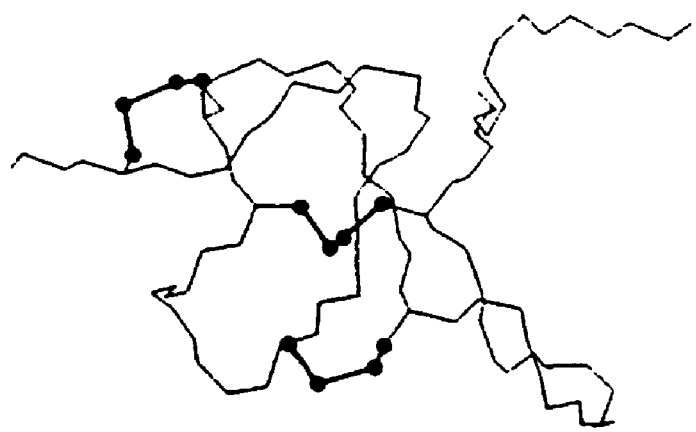
Figure 2:
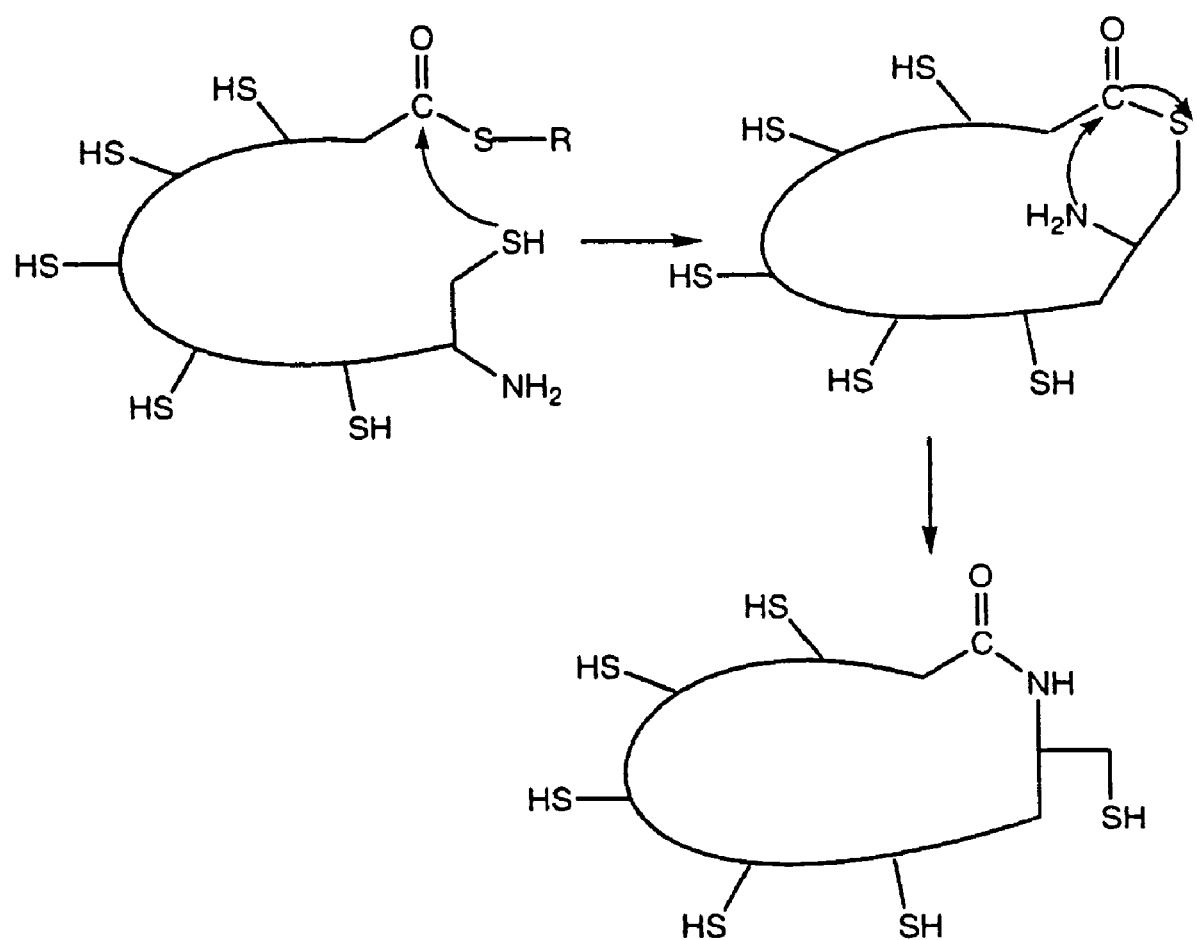
Figure 3:
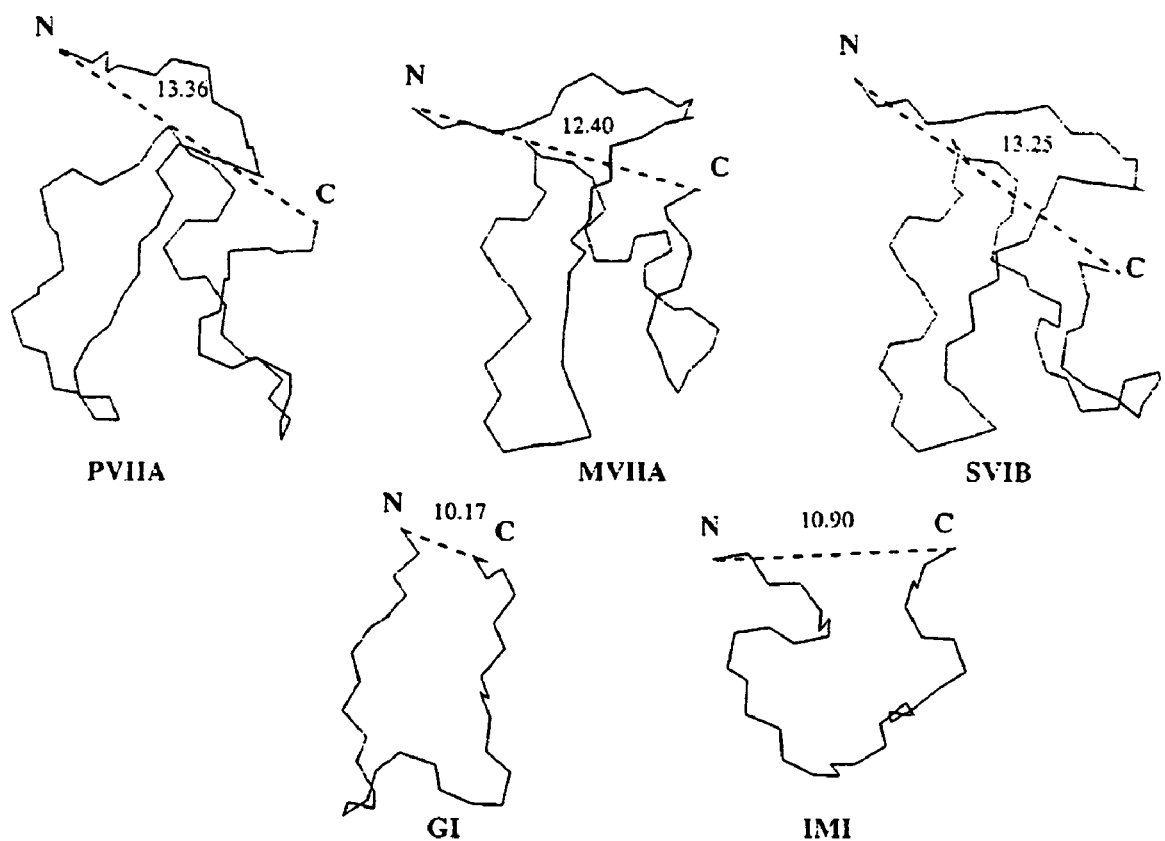
Figure 4:
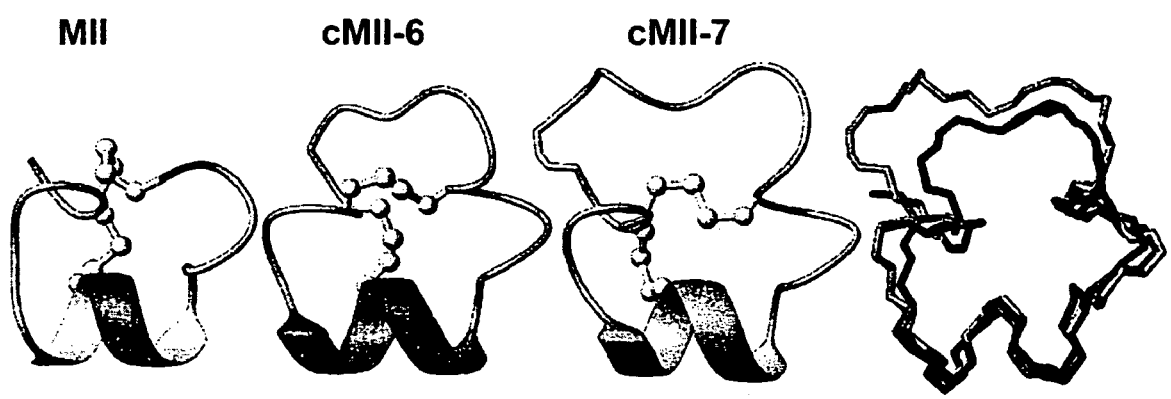

The three-dimensional structures of several conotoxin peptides have been determined by NMR spectroscopy to confirm the feasibility of making cyclised conotoxins which do not significantly alter the conformation of most parts of the conotoxin molecules. A comparison of five conotoxin structures determined by NMR is presented in FIG. 3.

Only the backbone atoms are displayed and the amino and carboxy termini are labelled as N and C respectively. The distances in angstroms between the termini have been measured and are also marked on the diagram. The three structures in the top half of the diagram represent PVIIA (Scanlon et al., 1997), MVIIA (Nielsen et al., 1996) and SVIB (Nielsen et al., 1996). It is clear that in all three peptides the overall structure is very similar, as is the distance between the termini. MVIIA and SVIB are both classed as omega conotoxins and have some sequence homology (Table 1), however PVIIA belongs to the kappa class and has little sequence homology to MVIIA and SVIB except for the conserved cysteine residues. It has now been shown that MVIIA can be cyclised and still retain a high level of activity (Examples 1-3). Given the structural similarity between the peptides mentioned above, cyclisation is equally feasible for other conotoxins belonging to the same O-superfamily, such as PVIIA and SVIB.

The alpha conotoxins have a different structure than the previously mentioned peptides, however the termini are still close, as shown for GI (Gehrmann et al., 1998) and ImI (unpublished data) above. The close proximity of the termini suggests cyclisation can be achieved without significantly affecting the biological activity. Thus, the concept of cyclising conotoxins is applicable not only to omega conotoxins but to peptides from other classes of conotoxins, including alpha and kappa, and extends to all conotoxins which have termini located close together, especially those within a distance of approximately 13 Å (i.e. the distance present in MVIIA).

In the case of mu-conotoxins the termini are further apart in general, but cyclisation is readily possible using longer peptide sequences as linkers. In the case of Na-channel conotoxins like GS the peptide contains a C-terminal extension beyond the final cysteine residue that may form part of the cyclising linker.

Example 5

To exemplify the principles involved in synthetic method 2 described above an analogue of MVIIA has been synthesised using solid phase peptide synthesis with Boc chemistry. The synthesised peptide has the sequence:

GLPVCKGKGAKCSRLMYDCCTGSCRSGKCTRG

SEQ ID NO.7

The peptide has both an N(GLPV) (SEQ ID NO. 38) and C(TRG) (SEQ ID NO. 39) terminal extension and the remaining residues (in bold) represent MVIIA. The reduced peptide was purified using the conditions given in Examples 1 and 2. Oxidation was achieved using 0.1M ammonium acetate, 2M ammonium sulfate, pH 7.7, 1 mM reduced glutathione and the reaction left at 4° C. for two days. The oxidised peptide was purified and the activity tested as in Example 3. An $EC_{50}$ of $1.081 \times 10^{-9}$ M was found for this analogue, illustrating that extending the N and C termini of the peptide, as may be necessary prior to cyclisation, does not eliminate activity.

Example 6

A cyclic α-conotoxin is prepared based on the sequence of α-contoxin MII. The linear precursor for this synthesis is designed by first adding a linker moiety to the native sequence as shown below. The residues in bold correspond to the native sequence of MII and the non-bold residues are the linker moiety (TNG) (SEQ ID NO. 4).

GCCSNPVCHLEHSNLCTNG

SEQ ID NO.8

A cyclically permuted derivative of this sequence is then designed by moving the N-terminal glycine residue to the C-terminus to produce the sequence:

CCSNPVCHLEHSNLCTNGG

SEQ ID NO.9

This peptide is synthesised using the thioester method described above in which the C-terminal glycine is attached to a Gly PAM resin via a —SCH$_2$CH$_2$CO— linker. The linker is attached to the Gly PAM resin by treating the resin with bromopropanoic acid for 30 minutes, washing with DMF and then treating the resin with 10% thioacetic acid, 10% DIEA in DMF for 2×20 minutes. The resin is washed again with DMF and treated with 10% β-mercaptoethanol, 10% DIEA in DMF for 2×20 minutes. After a final wash with DMF, the first (ie C-terminal) residue of the linear peptide sequence is coupled to the resin using HBTU and DIEA. The remainder of the peptide sequence is assembled by manual synthesis using HBTU with in situ neutralisation. Cleavage from the resin, cyclisation and oxidation is achieved using the methods described in Examples 1 and 2.

Example 7

The bioavailability of cyclic conotoxins is tested by either oral administration or intravenous administration into rats. Male Sprague-Dawley-derived rats (ca. 325 g) are maintained on standard rat pellets until surgery, and are subsequently prepared, under isoflurane anaesthesia, with a catheter in the right external jugular vein. Rats are then placed unrestrained n metabolism cages and allowed to recover prior to dosing. A 75 mm oral dosing (gavage) needle is used to dose conscious rats and the jugular catheter is used for iv dosing. Following dosing, plasma samples are taken out at time points between 0 and 180 min. A blood sample (ca. 500 mL) is withdrawn and centrifuged and then placed on ice until processing. The supernatant (200 mL) is transferred and HPLC grade acetonitrile (300 mL) added to precipitate proteins, however the test peptides remain in solution. The sample is then centrifuged and the supernatant transferred for further analysis. The supernatant is diluted with 0.1% TFA and injected on to an analytical reverse phase C18 column using gradients of 0.1% TFA/0.9% TFA in 90% acetonitrile 10% water. The eluent is monitored at 214 nm. This analysis allows calculation of a half-life for the peptide of interest.

Further studies are performed to give indications of stability of cyclised conotoxins in biological media and hence an indication of bioavailability. Biological media such as fetal calm serum and rat gastric juices are used. The cyclic conotoxin solution (10 mL/mg/mL) is diluted with 0.1 M PBS pH 7.6 (~50 mL) and fetal calm serum (~50 mL) is added to the sample. The sample is then incubated at 37° C. for ~1-5 hours. An aliquot (~40 mL) is removed and diluted with 0.1% TFA and injected on an analytical C18 reverse phase HPLC column with gradients of 0.1% TFA/0.9% TFA in acetonitrile. The sample is monitored at 214 nm. The stock peptide solution, appropriately diluted, is used as a control and allows the percentage breakdown at a particular timepoint to be calculated. A similar protocol is applied for rat gastric juices. However, the peptide is not diluted in buffer but incubated at 37° C. for 1-5 hours and aliquots analyzed by reverse phase HPLC. Performing these studies on linear and cyclic conotoxins shows the greater stability of the cyclic conotoxins.

Example 8

Cyclic MII Analogues (a) Design and Synthesis

The size of the linker required to span the N and C tennini of the native MII peptide was determined using well-known molecular modelling methodology. The three-dimensional model of MII was downloaded from the Protein Data Bank (PDB). The molecular modelling program, Accelrys (Insight II Modeling Environment, Release 2000, San Diego, Accelrys Inc. 2001), was used to determine an appropriate linker length. Briefly, this involved building in an amino acid linker between the N- and C-termini, then locking the conformation of the parent conotoxin structure and performing a simple energy minimisation. The conformation of the parent conotoxin was then unlocked and the entire peptide structure reminimized. Models with a linker size that is too small result in structures with higher energies than those with a linker length that does not perturb the native structure. It was determined that a linker containing a minimum of five residues was required to span the N- and C-termini. Therefore peptides containing linkers of five (GGAAG) (SEQ ID NO. 40), six (GGAAGG) (SEQ ID NO. 41) and seven (GGAGAAG) (SEQ ID NO. 42) residues in addition to the N-terminal glycine were synthesised. This corresponds to a total intercysteine length spanning six to eight residues. Distance measurements revealed that each residue in the linker would need to span approximately 2.0 to 2.4 angstroms (note that this is less than an extended conformation which would span approximately 3.5 angstroms and therefore represents a relaxed conformation). Glycines and alanines were chosen for the linker amino acids as they are relatively inert amino acids with small side-chains that are less likely to interact with other residues in the native peptide, or interfere with folding compared to larger or highly functionalised amino acid residues.

(b) Synthesis of Cyclic MII Analogues

The peptides were synthesised using BOC/HBTU chemistry with in situ neutralisation utilising a thioester linker (Schnölzer, M., Alewood, P., Jones, A., Alewood, D. and Kent, S. B. H. (1992) Int. J. Pept. Protein Res. 40, 180-193; Dawson, P. E., Muir, T. W., Clark-Lewis, I. and Kent, S. B. (1994) Science 266, 776-9; Tam, J. P., Lu, Y. -A. and Yu, Q. (1999) J. Am. Chem. Soc. 121, 4316-4324; Yan, L. Z. and Dawson, P. E. (2001) J Am Chem Soc 123, 526-33).

This linker was synthesised by treating Gly PAM resin with 4 equivalents of S-trityl-β-mercaptopropionic acid, 4 equivalents of HBTU and 5 equivalents of DIEA in DMF (2×30 minutes). The trityl group is then removed by treating the resin with TFA/triisopropylsilane/$H_2O$ (96:2:2) for 2×20 minutes. The C-terminal residue of the peptide chain was then added to the linker using standard coupling conditions. Alternatively, the linker can be assembled using the methodology described in the example 1. Peptides with a C-terminal thioester can also be made using FMOC chemistry by following standard literature procedures [Ingenito, R., Bianchi, E., Fattori, D. and Pessi, A. (1999) J Am Chem Soc 121, 11369-74; Shin, Y., Winans, K. A., Backes, B. J., Kent, S. B. H., Ellman, J. A. and Bertozzi, C. R. (1999) J Am Chem Soc 121, 11684-89; Clippingdale, A. B., Barrow, C. J. and Wade, J. D. (2000) J Pept Sci 6, 225-34; Camarero, J. A., Hackel, B. J., De Yoreo, J. J. and Mitchell, A. R. (2004) J Org Chem 69, 4145-51]. Once the peptide chain was assembled it was cleaved from the resin using the method described in Example 1. The crude peptide mixture was then purified by RP-HPLC utilising a gradient of 0-80% B over 80 minutes (A=0.05% TFA in water, B=90% acetonitrile, 9.95% water, 0.05% TFA) using a $C_{18}$ column. Fractions were collected, analysed by MS and those containing the desired product were pooled and lyophilised.

Oxidation and cyclisation of the purified linear reduced peptide was achieved by dissolving the peptide in either 0.1M $NH_4HCO_3$ (pH 8.1) or 50/50 0.1M $NH_4HCO_3$/iPrOH at a concentration of approximately 0.3 mg/mL. The reaction mixture was stirred overnight at room temperature and the resulting mixture purified by RP-HPLC using the conditions described above. The peptides have the sequence given below.

The six residue linker cyclic MII formed two distinct isomers in an approximate ratio of 45:55. In contrast, the crude oxidation HPLC profile of the five residue linker cyclic MII appeared as a poorly dispersed set of peaks. Finally, the seven residue linker cyclic MII formed one predominant (>90%) isomer which, from the $^1$H NMR data, had a well ordered structure. The small number of peaks in the crude oxidation mixture for the MIII analogues with a linker size of six residues (in addition to the N-terminal glycine) provides a preliminary indication that this is the optimal minimal size for MII. For the crude mixtures, individual peaks were collected and analysed by MS. Those containing peptides of a mass corresponding to the cyclised and oxidised peptide were subjected to analytical RP-HPLC. Fractions were then combined based on the HPLC analysis and lyophilised.

The 1D $^1$H NMR spectrum of the cyclic peptides obtained in sufficient amounts were measured. One isomer of the five residue linker peptide appeared to have a well-ordered structure based on the $^1$H NMR spectrum. In the case of the six residue linker peptide the later eluting, more abundant isomer appeared well ordered based on the $^1$H NMR spectrum. The seven residue cyclic MII peptide was also well ordered based on the $^1$H NMR spectrum.

The sequence of the cyclic peptide analogues of MII are shown below:

(a) cMII-5

Gly Cys Cys Ser Asn Pro Val Cys His Leu Glu His Ser Asn Leu Cys Gly Gly Ala Ala Gly

SEQ ID NO.10

(b) cMII-6

Gly Cys Cys Ser Asn Pro Val Cys His Leu Glu His Ser Asn Leu Cys Gly Gly Ala Ala Gly Gly

SEQ ID NO.11

(c) cMII-7

Gly Cys Cys Ser Asn Pro Val Cys His Leu Glu His Ser Asn Leu Cys Gly Gly Ala Gly Ala Ala Gly

SEQ ID NO.12

(c) Structural Characterisation of the Cyclic MII Analogues

Two-dimensional NMR spectral data were then obtained for the three well ordered analogues (now referred to as cMII-5, cMII-6 and cMII-7). A complete NMR assignment was made and the chemical shift of the Hα and $H_N$ protons was compared to those of native MII. A comparison of chemical shift data gives an indication of how similar the structures are. The results revealed that the chemical shifts of cMII-5 were poorly matched to those of MII, indicating a change in structure. In contrast, the chemical shifts of cMII-6 and cMII-7 were highly correlated to those of the native conotoxin. This indicates that cMII-6 and cMII-7 adopt a similar structure to native MII, whereas cMII-5 clearly deviates from the native structure.

From this it was evident, based on the oxidation profile and the NMR data, that a linker of five added residues was too short and interfered with the correct folding of the conotoxin while a linker with six or seven added residues was of sufficient size to allow the cyclic analogue to form a native-like structure. The full three dimensional (3D) structures of both cMII-6 and cMII-7 was determined to confirm the close correlation of structure between the native MII and their cyclic counterparts.

The 3D structure of cMII-6 was determined using NMR spectroscopy. Spectra were obtained on a Bruker DMX 750 spectrometer at 280 and 287 K. The homonuclear spectra recorded included double quantum filtered DQF-COSY [Rance, M., Sørensen, O. W., Bodenhausen, G., Wagner, G., Ernst, R. R. and Wüthrich, K. (1983) Biochem. Biophys. Res. Commun. 117, 479-485.], TOCSY using a MLEV17 spin lock sequence [Bax, A. and Davis, D. G. (1985) J. Magn. Reson. 65, 355-360.] with an isotropic mixing time of 80 ms; ECOSY [Griesinger, C., Sørensen, O. W. and Ernst, R. R. (1987) J. Magn. Reson. 75, 474-492], and NOESY [Jeener, J., Meier, B. H., Bachmann, P. and Ernst, R. R. (1979) J. Chem. Phys. 71, 4546-4553; Kumar, A., Ernst, R. R. and Wüthrich, K. (1980) Biochem. Biophys. Res. Commun. 95, 1-6] with mixing times of 150 and 350 ms. In DQF-COSY and ECOSY experiments, the water resonance was suppressed by low power irradiation during the relaxation delay. For the TOCSY and NOESY experiments, water suppression was achieved using a modified WATERGATE sequence [Piotto, M., Saudek, V. and Sklenar, V. (1992) J. Biomol. NMR 2, 661-665]. Two-dimensional spectra were generally collected over 4096 data points in the f2 dimension and 512 increments in the f1 dimension over a spectral width corresponding to 12 ppm. For identification of slowly exchanging amides, a series of one-dimensional and TOCSY spectra were run immediately after dissolving the sample in $D_2O$. All spectra were processed on a Silicon Graphics workstation using XWINNMR (Bruker). The f1 dimension was zero-filled to 2048 real data points with the f1 and f2 dimensions being multiplied by a sine-squared function shifted by 90° prior to Fourier transformation. Processed spectra were analyzed and assigned using the program XEASY [Eccles, C., Guntert, P., Billeter, M. and Wüthrich, K. (1991) J. Biomol. NMR 1, 111-30]. Spectra were assigned using the sequential assignment protocol [Wüthrich, K. (1986) Wiley-Interscience, New York]. The process was facilitated, in part, using the automatic assignment program NOAH, which is part of the DYANA package [Guntert, P., Mumenthaler, C. and Wüthrich, K. (1997) J. Mol. Biol. 273, 283-98]. Cross-peaks in NOESY spectra recorded in 90% $H_2O$, 10% $D_2O$ with mixing times of 350 and 150 ms were integrated and calibrated in XEASY, and distance constraints were derived using DYANA. Backbone dihedral angle restraints were derived from $^3J_{HNH\alpha}$ coupling constants measured from line shape analysis of antiphase cross-peak splitting in the DQF-COSY spectrum. Angles were restrained to −120°±30° for $^3J_{HNH\alpha}>8.5$ Hz and to −60°±30° for $^3J_{HNH\alpha}<5$ Hz. Stereospecific assignments of β-methylene protons and χ1 dihedral angles were derived from $^3J_{\alpha\beta}$ coupling constants, measured from ECOSY spectra, in combination with NOE peak intensities. Preliminary structures were calculated using a torsion angle simulated annealing protocol within DYANA. Final structures were calculated using simulated annealing and energy minimization protocols within CNS version 1.0 [Brünger, A. T., Adams, P. D. and Rice, L. M. (1997) Structure 5, 325-336]. The starting structures were generated using random phi, psi dihedral angles and energy-minimized to produce structures with the correct local geometry. This protocol involves a high temperature phase comprising 4000 steps of 0.015 ps of torsion angle dynamics, a cooling phase with 4000 steps of 0.015 ps of torsion angle dynamics during which the temperature was lowered to 0 K, and finally an energy minimization phase comprising 5000 steps of Powell minimization. Structures were refined using further molecular dynamics and energy minimization in a water shell, as described by Linge and Nilges [Linge, J. P. and Nilges, M. (1999) J. Biomol. NMR 13, 51-9]. The refinement in explicit water involves the following steps. First heating to 500 K via steps of 100 K, each comprising 50 steps of 0.005 ps of Cartesian dynamics. Second, 2500 steps of 0.005 ps of Cartesian dynamics at 500 K before a cooling phase where the temperature was lowered in steps of 100 K, each comprising 2500 steps of 0.005 ps of Cartesian dynamics. Finally, the structures were minimized with 2000 steps of Powell minimization. Structures were analyzed using Promotif and Procheck [Hutchinson, E. G. and Thornton, J. M. (1996) Protein Sci. 5, 212-220; Laskowski, R. A., Rullmannn, J. A., MacArthur, M. W., Kaptein, R. and Thornton, J. M. (1996) J. Biomol. NMR 8, 477-86].

A comparison of cMII-6 with MII show native conformation of MII is retained in toto in cMII-6. The striking degree of similarity between the two peptides is illustrated in FIG. 4.

(d) Selective Synthesis of cMII-6

Although non-selective oxidation is the preferred method used in the synthesis of cyclic conotoxins, they can also be made using directed disulfide bond formation as demonstrated for cMII-6. The peptide was synthesised as described above but the sidechains of cysteines 3 and 16 were protected with Acm groups. The peptide was cleaved from the resin, purified and oxidised/cyclised using the conditions described above. The second disulfide bond was formed selectively between cysteines 3 and 16 by deprotection/oxidation using $I_2$. The peptide (20 mg) was dissolved in 50% aqueous acetic acid at a concentration of 1 mg/mL and the flask flushed with nitrogen. To the flask was added 2 mL of 1M HCl followed by sufficient 0.1M $I_2$ in 50% aqueous acetic acid to make the solution a pale. yellow (approximately 1 mL). The reaction was then stirred under nitrogen at room temperature for 1.5 hours. The reaction was quenched by the addition of 1M ascorbic acid until the reaction mixture became colourless. The mixture was then diluted with buffer A and purified by RP-HPLC to yield the cyclic, fully oxidised peptide. This peptide co-eluted with cMII-6 and hence confirmed the disulfide connectivity of cMII-6 as corresponding to that of the native peptide ie., Cys2-Cys8 and Cys3-Cys16 (1-3, 2-4).

(e) Biological Activity of cMII-6

Figure 5:
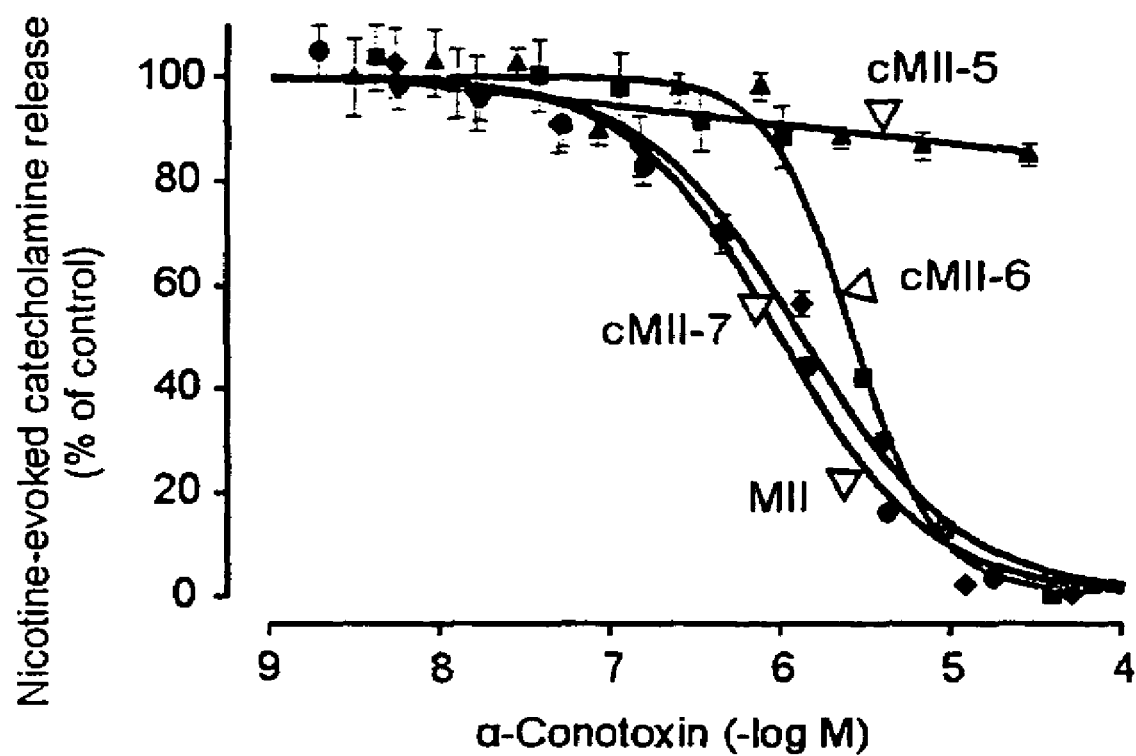
FIG. 5 is a graph depicting the concentration-response curves for inhibition of nicotine (5 μM)-evoked catecholamine release from isolated bovine chromaffin cells by increasing concentrations of MII, cMII-5, cMII-6 and cMII-7. The results indicate that the activity of the cyclic peptides is comparable to linear MII.

Chromaffin cells were prepared from bovine adrenal glands and maintained in 24-well plates (Nunc) as described in standard literature procedures [Lawrence, G. W., Weller, U. and Dolly, J. O. (1994) Eur J Biochem 222, 325-33; Meunier, F. A., Mattei, C., Chameau, P., Lawrence, G., Colasante, C., Kreger, A. S., Dolly, J. O. and Molgo, J. (2000) J Cell Sci 113 (Pt 7), 1119-25; Meunier, F. A., Feng, Z. P., Molgo, J., Zamponi, G. W. and Schiavo, G. (2002) Embo J 21, 6733-43.]. Intact cells were washed briefly once with buffer A (mM): NaCl, 145; KCl, 5, $Na_2HPO_4$, 1.2; glucose, 10; HEPES-NaOH, 20 (pH 7.4) and incubated with native and cyclised conotoxins for 20 min in the presence of 2 mM $CaCl_2$ and stimulated by nicotine (5 µM) for 20 min. Aliquots of the supernatant were taken at the end of each experiment and cells were lyzed with 1% (v/v) Triton X-100 (Sigma). Both sets of samples were assayed fluorimetrically for catecholamines, and the amount released expressed as a percentage of control as described in the literature (see above). The results of the biological assay are shown in FIG. 5 and indicate that the activity of the cyclic peptides are comparable to that of linear MII.

(f) Stability of cMII-6

The stability of cMII-6 against attack by proteolytic enzymes was assessed by incubating the peptide with endoproteinase Glu-C (Endo Glu-C). Both MII and cMII-6 have an identical potential processing site, on the opposite face from the ternini (in MII) and the linker (in cMII-6). The peptides were dissolved in 0.1M $NH_4HCO_3$ (pH 8.0) buffer at a concentration of 20 µg/mL. Endo GluC was then added at a peptide:enzyme ratio (wt/wt) of 50:1 and the solution incubated at 37° C. Aliquots (3 µL) were taken out and quenched with 5% formic acid (57 µL) every hour from 0-10 plus after 24 hours. Samples were then analysed by LC/MS and the amount of intact peptide remaining at each time point determined. Each trial was performed in triplicate with the appropriate positive (a linear non-disulfide peptide with a EndoGluC cleavage point) and negative (peptide in buffer with no enzyme) controls.

Figure 6:
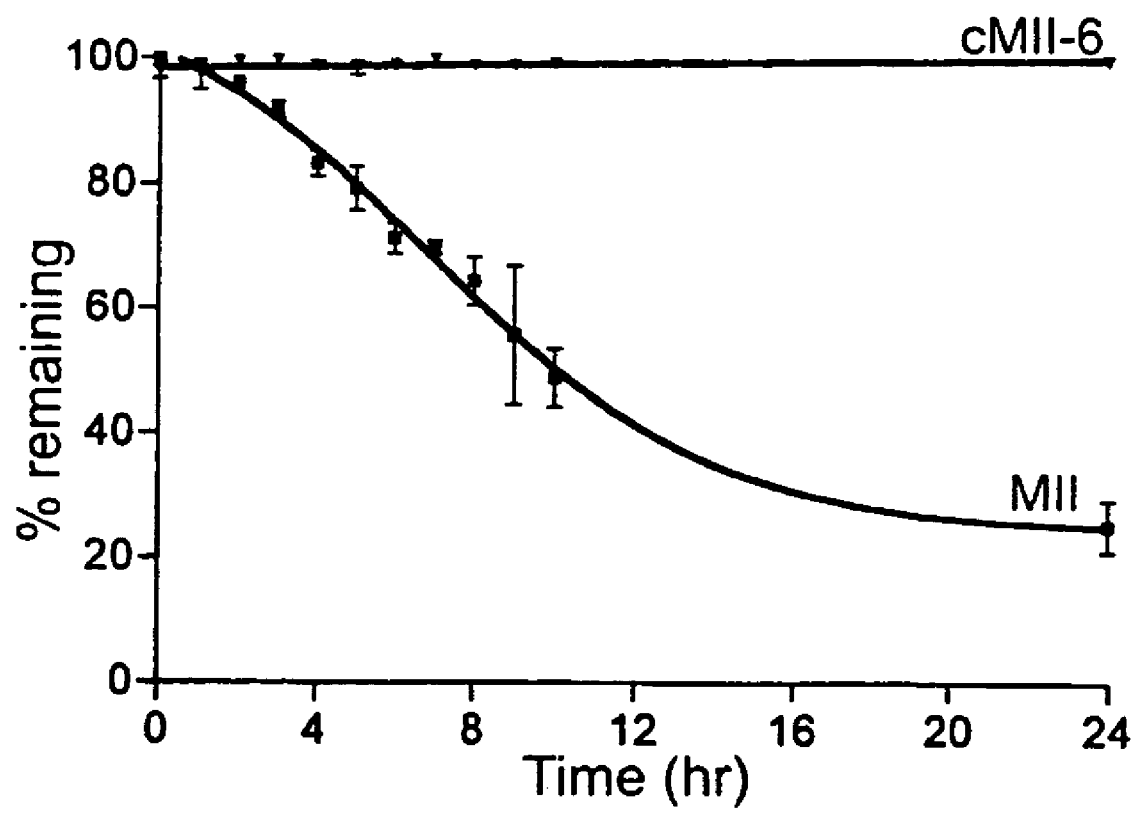
FIG. 6 is a graph depicting the relative stability of MII and cMII-6 against attack by proteolytic enzymes as assessed by incubating the peptide with endoproteinase, Endo-GluC. The amount of intact peptide remaining was determined by RP-HPLC.

The results of the stability assay are illustrated in FIG. 6. The cyclic peptide remains entirely intact over the full 24 hour period whereas native MII has a half life of approximately 10 hours. The enhanced stability demonstrated by cMII-6 is surprising given that the putative processing sites on MII and cMII-6 are identical (ie., on the C-terminal side of Glutamic Acid) and distant from the termini (in MII) and the peptide linker in cMII-6. Additionally, it may be expected that any enhanced stability would be against only against exoproteases that are active against the N-terminus (MII is amidated at its C-terminus), yet Glu-C is an endoprotease. Thus, the cyclic conotoxins appear to have enhanced stability beyond that which may be expected from protection of the termini alone.

(g) Stability of cMII-6 and cMII-7 against Enzymes in Human Plasma

To test the resistance of cMII-6 and cMII-7 against proteolytic attack, and compare this with MII, these conotoxins were incubated in human blood plasma. MII, cMII-6 and cMII-7 (10 µM) were incubated in 50% human plasma for a period of 24 hours. Aliquots were taken at several time points, quenched with 15% aqueous trichloroacetic acid and centrifuged. The supernatant was then analysed by RP-HPLC.

Figure 7:
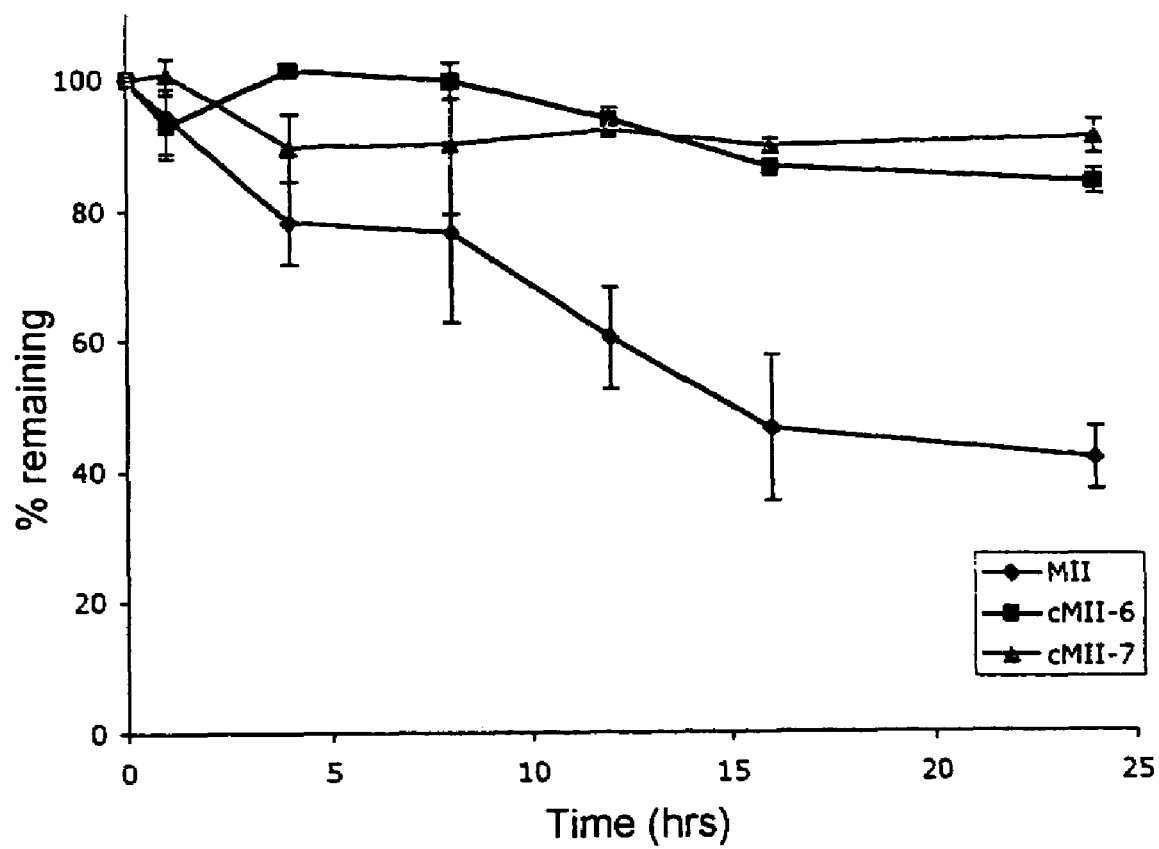
FIG. 7 is a graph depicting the relative stability of MII, cMII-6 and cMII-7 against enzymes in 50% human plasma. The amount of intact peptide remaining was determined by RP-HPLC.

Each trial was performed in triplicate. FIG. 7 shows the results of this experiment. The stability of cMII-6 and cMII-7 is dramatically greater than MII. Native MII had a half-life of approximately 16 hours whereas the amount of cMII-6 and cMII-7 remaining after 24 hours was close to 90%.

Example 9

Synthesis and Characterisation of Cyclic Vc1.1

(a) Design of Cyclic Vc1.1

The α-conotoxin Vc1.1 is a member of the 4/7 class of α-conotoxins which includes MII, and has potential for the treatment of pain (Sandall D W, Satkunanathan N, Keays D A, Polidano M A, Liping X, Pham V, Down J G, Khalil Z, Livett B G, Gayler K R, Biochemistry 2003 42(22):6904-11). There is no structural data available for Vc1.1 in the literature and hence the procedure described above for the design of the cyclic MII analogues could not be followed. However, because other conotoxins with this same framework have been studied structurally, it was possible to estimate the optimal linker length for Vc1.1 by simple distance measurements on other members of the same family, including MII and PnIA. There are four structures of α4/7 conotoxins in the Protein Data Bank excluding duplicate structures and the conotoxin GID which has an extended flexible "tail" on the N-terminus. By averaging the distance between the N- and C-termini of these structures of these four compounds the value obtained is quite consistent (12.2±0.8 Å). Therefore it can be estimated that suitable linker lengths for cyclising Vc1.1 would be similar to those used for cyclising MII. eg. approximately six to seven residues. Again, these six residues are additional to an existing Glycine residue at the N-terminus.

(b) Synthesis and Structural Characterisation of Cyclic Vc1.1 and Vc1.1

The synthesis of cyclic Vc1.1 was carried out using the synthetic procedures described for cyclic MII (example 8). The cyclisation/oxidation buffer used for cyclic Vc1.1 was 0.1M $NH_4HCO_3$ (pH 8.1). The cyclisation/oxidation yielded one predominant isomer (now referred to as cVc1.1-6) that was purified and analysed by $^1H$ NMR spectroscopy. The sequence of Vc1.1 (which is C-terminally amidated) and cVc1.1-6 are shown below.

Gly Cys Cys Ser Asp Pro Arg Cys Asn Tyr Asp His Pro Glu Ile Cys

SEQ ID NO.13

Gly Cys Cys Ser Asp Pro Arg Cys Asn Tyr Asp His Pro Glu Ile Cys Gly Gly Ala Ala Gly Gly

SEQ ID NO.14

Linear Vc1.1 was also synthesised using BOC/HBTU chemistry with in situ neutralization on MBHA-amide resin. The peptide was folded in 0.1M NH$_4$HCO$_3$ at room temperature overnight and yielded a single isomer. The disulfide connectivity of synthetic Vc1.1 and cVc1.1-6 were both confirmed to be Cys2-Cys8, Cys3-Cys16 using standard reduction/alkylation methodologies [Göransson, U. and Craik, D. J. (2003) J. Biol. Chem. 278, 48188-96]. with MS/MS sequencing. The three dimensional NMR structure was then determined for comparison to cVc1.1-6. The three dimensional structure of both Vc1.1 and cVc1.1-6 was determined using NMR spectroscopy as described above for cyclic MII. The native conformation of Vc1.1-6 is retained in cVc1.1-6 as shown in FIG. 8.

(c) Biological Activity of cVc1.1-6

The biological activity of cVc1.1-6 was analysed by measuring catchecholamine release from bovine adrenal chromaffin cells as described for the cyclic MII example. The results of the assay are shown in FIG. 9 which demonstrates that the activity of cVc1.1-6 is identical, within experimental error, to that of acyclic Vc1.1.

(d) Stability of cVc1.1-6

The ability of cVc1.1-6 to resist attack by proteolytic enzymes can be assessed using the experiments outlined for cyclic MII. Resistance to breakdown in mammalian gastric juices and plasma can also be assessed using the protocols given in examples 7 and 8.

Example 10

Synthesis and Characterisation of Cyclic MrIA (a) Synthesis of Cyclic MrIA

Cyclic MrIA (cMrIA-AG) was synthesised using a native chemical ligation strategy. This methodology involves an intramolecular reaction between an N-terminal Cys residue and a C-terminal functionalised by a thioester moiety to give a cyclic peptide with a native amide bond. The synthesis of cMrIA-AG was achieved according to Scheme 1.

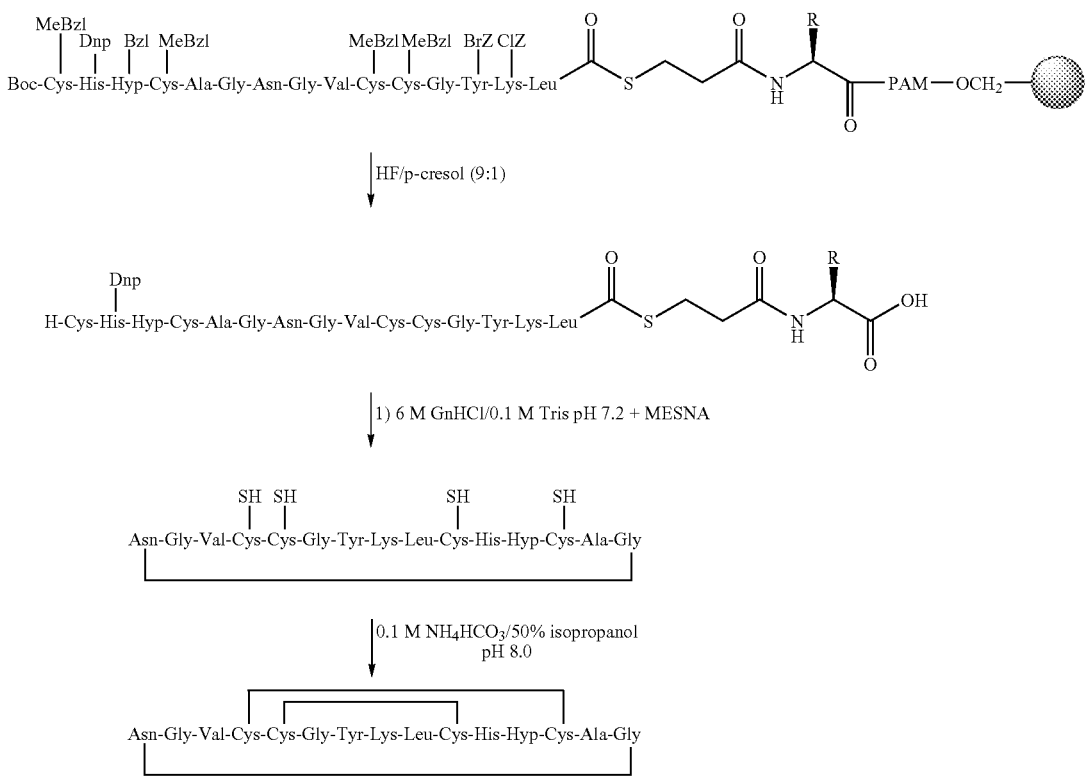

Scheme 1: Synthetic strategy for the preparation of cMrIA-AG (SEQ ID NO. 43 → SEQ ID NO. 43 → SEQ ID NO. 44 → SEQ ID NO. 44)

The linear thioester precursor was synthesised on a 0.25 mmol scale on a thioester resin. The thioester linker was prepared by coupling S-tritylmercaptopropionic acid to Boc-Gly-OCH$_2$ PAM resin using HBTU. Removal of the S-trityl group was achieved using 5% TIPS in TFA (2×1 min) and the C-terminal amino acid amino acid coupled with HBTU. The sequence was assembled using Boc in situ neutralisation protocols with HBTU mediated couplings. As the thioester linker is not compatible with thiol treatments, the dinitophenyl group on histidine (His(Dnp)) was not removed with 2-mercaptoethanol prior to HF cleavage. Cleavage of the linear thioester peptide from the resin was achieved by treatment with HF/p-cresol for 2 hours at 0° C. to give the linear thioester precursor.

Cyclisation was performed by dissolving the linear thioester precursor in aqueous buffer consisting of 6 M GnHCl/0.1 M tris, pH 8.0 containing 1 mg/mL of 2-mercaptoethanesulfonic acid sodium salt (MESNA). The buffer was degassed with argon prior to addition of the peptide and all operations were performed under a blanket of argon. Inclusion of MESNA accelerated the cyclisation process through thioester transfer and also effected the removal of His(Dnp). The reaction was monitored by analytical RP-HPLC and was complete after 7 hours. The reduced cyclic peptide was isolated by semi preparative RP-HPLC.

cMrIA-AG was oxidised by stirring the cyclic reduced peptide in 0.1 M $NH_4HCO_3$/50% isopropanol, pH 8.2 in an open vessel and monitored by RP-HPLC and LC-MS. After the oxidation was complete after 8 hours, the mixture was acidified to pH 2 using TFA and the isopropanol was evaporated in vacuo. The final peptide product was isolated using semi-preparative RP-HPLC. 3.5 mg of cMrIA-AG was obtained in high purity.

The sequence of the native Mr1A and the cyclic Mr1A are shown below:

```
Asn Gly Val Cys Cys Gly Tyr Lys Leu Cys His Hyp Cys
                SEQ ID NO. 15
Asn Gly Val Cys Cys Gly Tyr Lys Leu Cys His Hyp Cys Ala Gly
|_____|

SEQ ID NO. 16
```

(b) Structure Determination of Cyclic MrIA

The 3D structure of cyclic MrIA was determined using NMR spectroscopy as described in example 8 for cyclic MII. The native conformation of MrIA is retained in cyclic MrIA as shown in FIG. 10.

The disulfide bond connectivities can be determined readily by comparison of the deviations from experimental parameters for structures calculated separately with the different possible combinations. The results are given in Table 3. The set of structures with the Cys 1-4 and Cys 2-3 connectivity exhibit significantly lower energies than the other two possible combinations. This provides compelling evidence that the cyclic conotoxin has the same disulfide connectivity as the native conotoxin.

TABLE 3

| Energies | Disulfide connectivity | | |
|---|---|---|---|
| | Cys 1-4, Cys 2-3 | Cys 1-2, Cys 3-4 | Cys 1-3, Cys 2-4 |
| NOE | 22.2 ± 3.08 | 67.4 ± 7.6 | 91.0 ± 7.5 |
| Dihedral angle | 0.9 ± 0.31 | 6.5 ± 1.5 | 11.5 ± 2.7 |

The above table sets out a comparison of the energetics from structures calculated with the three possible disulfide connectivities for cyclic MrIA. The NOE and dihedral energies are shown for the three connectivities.

(c) Biological Assay: Human Noradrenaline Transporter Radio Ligand Binding Assay Cyclic MrIA and MrIA were assayed as described in Sharpe et al [Sharpe, I. A., Palant, E., Schroeder, C. I., Kaye, D. M., Adams, D. J., Alewood, P. F. and Lewis, R. J. (2003) J Biol Chem 278, 40317-23] using membranes from COS-7 cells transfected with human NET using metafectene reagent. Membranes were incubated with [$^3$H] nisoxetine in the absence or presence of cyclic MrIA. The $EC_{50}$ of MrIA and cyclic MrIA are given in Table 4 and are illustrated in FIG. 12. was $1.47 \times 10^{-6}$ M and the $EC_{50}$ of cyclic MrIA was $9.90 \times 10^{-7}$ M.

TABLE 4

Binding of χ-conotoxin MrIA analogues at the human NET expressed in Cos-7 cells.

| Analogue | log $EC_{50}$ | $EC_{50}$ |
|---|---|---|
| MrIA-NH$_2$ | −5.74 | 1.81 ± 0.19 μM |
| cMrIA-AG | −5.19 | 6.46 ± 1.17 μM |

(d) Stability Assays

The susceptibility of MrIA and cyclic MrIA to trypsin was analysed by incubating the peptides in 0.1 M ammonium bicarbonate at pH 8 with a 1:20 ratio of trypsin to peptide. Aliquots were removed at timepoints between 1 min and 24 hours and the reaction quenched by acidification with 0.5% formic acid. The aliquots taken for each timepoint were analysed using mass spectrometry to determine the extent of cleavage with trypsin. The reactions were performed in triplicate. The percentage peptide remaining at each time-point was calculated by measuring peaks heights of the intact peptide and dividing by the sum of the peaks heights of the intact and degraded peptide.

The results, shown in FIG. 11, demonstrate that Cyclic MrIA is significantly resistant to cleavage by trypsin compared to the non-cyclic version. Again, this is a striking result, as it could not be anticipated that the stability of a cyclic contoxin would be extended to enhanced protection against endoproteases. The results also imply that this enhanced stability exhibited by cyclic conotoxins provides wide-ranging protection against proteases.

Example 11

Cyclic MrIA Using Selenocysteine (a) Introduction

Selenocysteine (Sec, or U) is often referred to as the $21^{st}$ amino acid. Despite the difference in chemical properties, mutation of cysteine to selenocysteine represents one of the most conservative substitutions that can be introduced into a peptide, since both exhibit very similar physical properties. The presence of two selenocysteine residues in a peptide chain allows the formation of diselenide bond, or a dimer with another peptide chain, which is analogous to the disulfide bond. Disulfides and diselenides both exhibit similar bond geometry, with a diselenide exhibiting a slightly longer bond length due to the larger size of the selenium atom.

It is well known that disulfide bonds play an important role in the conformational stability of many naturally occurring peptide hormones and animal toxins. However, substitution of disulfides with diselenides may impose interesting properties into a peptide molecule. For instance, diselenide bonds would be expected to exhibit increased stability in a reducing environment, such as the cytosol due to the increased redox potential. As many drugs mode of action often occur in a reducing environment, it would be expected that systematic replacement of cysteine with selenocysteine would result in increased stability.

Peptides containing an N-terminal selenocysteine will react with peptides containing a C-terminal thioester to form a selenoester intermediate under reducing conditions that spontaneously rearranges to give the more stable amide bond. Several selenoproteins have been chemically synthesised using this approach named selenocysteine mediated NCL. It is also well known that peptides possessing both an N-terminal cysteine and a C-terminal thioester can react to yield an N-to-C cyclic peptide. The selenocysteine mediated NCL approach (Quaderer and Hilvert) is used here for cyclic selenocysteine peptide containing analogues.

(b) Materials and Equipment

H-L-β-Chloroalanine was purchased from Bachem (Bubendorf, Switzerland), metallic selenium powder (200 mesh), sodium borohydride and tert butyloxycarbonyldicarbonate from Aldrich (Milwaukee, Wis.), p-methylbenzyl-chloride from Fluka (Buchs, Switzerland). TCEP was from Pierce (Rockford, Ill.). All solvents were of minimum analytical reagent grade. $^1$H NMR and $^{13}$C NMR spectra were recorded on a Varian 300 MHz Gemini spectrometer and chemical shifts are reported in parts per million (ppm) downfield from DSS in $D_2O$ or tetramethylsilane (TMS) in $CDCl_3$.

(c) Synthesis of Protected Selenocysteine Derivatives (i) Sodium Diselenide [$Na_2Se_2$]

Sodium borohydride (4.5 g, 119 mmol) in $H_2O$ (25 mL) was added drop wise to a stirred suspension of metallic selenium powder (4.5 g, 56 mmol) in $H_2O$ (25 mL) at 0° C. After the vigorous exothermic reaction had subsided and all the selenium had dissolved, additional selenium powder (4.5 g, 56 mmol) was added and the mixture stirred for a further 15 minutes at room temperature, then gently heated to aid dissolution of remaining selenium. The brown/red coloured solution was immediately used for subsequent reactions.

(ii) L-Selenocystine [(Sec)$_2$]

H-L-β-Cl-Ala-OH (5.0 g, 31 mmol) in $H_2O$ (40 mL) buffered to pH 9 with 0.1M NaOH was added drop wise over a period of 2 hours to a freshly prepared solution of sodium diselenide as described above. The solution was then stirred for 16 hours under argon at 37° C. before acidification to pH 2 with 6 M HCl. Hydroxylamine hydrochloride (0.330 g, 9.7 mmol) was added and the flask flushed with argon for 2 hours and the exhaust gas passed through two successive $NaOCl_4$ traps. The solution was then filtered through celite and the product precipitated by adjusting the pH to 6.5 using 6 M NaOH. The yellow solid was filtered, dried and dissolved in the minimum volume of 2 M HCl. Insoluble material which consisted mainly of elemental selenium was removed by filtration, then the product was precipitated by adjusting the solution to pH 6.5 and filtered to give an amorphous yellow solid (4.62 g, 70%). $^1$H NMR (300 MHz, $D_2O$+DCl+DSS) δ 4.5 (m, 1H), 3.5 (m, 2H); $^{13}$C NMR (75.4 MHz, $D_2O$+DCl+DSS) δ 168.8, 51.6, 25.3.

(iii) (4-methylbenzyl)-L-selenocysteine [H-Sec(MeBzl)-OH]

Selenocystine (3.80 g, 9.3 mmol) was dissolved in 0.5 M NaOH (15 mL). The solution was cooled to 0° C. and $NaBH_4$ (3.60 g, 11.4 mmol) added in small portions with stirring. After the exothermic reaction had subsided, the mixture was stirred until the solution became colourless (approximately 30 minutes). The solution was then carefully adjusted to pH 7 using 6 M HCl under a blanket of argon and then α-chloro-p-xylene (8 mL, 60 mmol) was added drop wise over 1 hour and then stirred for a further 2 hours at 0° C. under argon. The mixture was then acidified to pH 2 with 6 M HCl producing a white precipitate which was filtered, washed with diethyl ether (3×50 mL) and recrystallised from hot water to give 7.3 as a white crystalline solid (3.50 g, 61.1%). $^1$H NMR (300 MHz, $CD_3OD$+$D_2O$+DCl+DSS) δ 8.2 (d, 2H), 7.9 (d, 2H), 5.1 (m, 1H) 4.8, (s, 2H), 3.9 (m, 1H), 3.1 (s, 3H); $^{13}$C NMR (75.4 MHz, $CD_3OD$+$D_2O$+DCL) δ 170.7, 138.0, 136.8, 130.3, 130.1, 53.9, 28.7, 23.2, 21.4

(iv) N$^α$-tert-butyloxycarbonyl-(4-methoxybenzyl)-L-selenocysteine [Boc-Sec(MeBzl)-OH]

Se-(4-methoxybenzyl)-L-selenocysteine (3.24 g, 10 mmol) and $K_2CO_3$ (3.4 g, 0.15 mol) were dissolved in water (25 mL) with gentle heating. tert-Butyloxycarbonyl dicarbonate (2.30 g, 11 mol) in THF (25 mL) was added and the mixture stirred at room temperature for 1 hour before water (100 mL) was added. The mixture was washed with diethyl ether (2×100 mL) and the aqueous layer acidified to pH 4 with solid citric acid and extracted with ethyl acetate (3×100 mL). The combined extracts were washed with 10% citric acid (3×100 mL), brine (100 mL) and then dried over $MgSO_4$, filtered and solvent removed in vacuo to give Boc-Sec(MeBzl)-OH as a white crystalline solid which was recrystallised from petroleum spirits/diethyl ether. (2.8 g, 75.3%) $^1$H NMR (300 MHz, $CDCl_3$+TMS) δ 7.14 (d, 2H), 7.02 (d, 2H), 5.29 (d, 2H), 3.79 (m, 2H), 2.87 (s, 2H), 2.32 (s, 3H), 1.45 (s, 9H); $^{13}$C NMR (75.4 MHz, $CDCl_3$) δ 175.6, 155.4, 136.6, 135.4, 129.3, 128.8, 80.5, 53.3, 28.3, 27.8, 25.3, 21.1.

(d) Synthesis of Selenocysteine Derivatives of MrIA

The thioester resin was prepared by coupling S-tritylmercaptopropionic acid to Boc-Gly-OCH$_2$ PAM resin using HBTU, followed by removal of the S-trityl group using 5% TIPS in TFA (2×1 min) and subsequent double coupling of the C-terminal amino acid with HBTU. The linear thioester precursor peptide was assembled on a 0.25 mmol scale according to Boc in situ neutralisation protocols. Selenocysteine was incorporated into the peptide as a Se-4-methylbenzyl protected derivative. Boc-Sec(MeBzl)-OH was synthesised from H-L-β-chloroalanine as described in above and incorporated into the peptide using 2 equivalents of amino acid rather than the usual 4 equivalents. As the thioester linker is not compatible with thiol treatments, the dinitophenyl group on histidine (His(Dnp)) was not removed with 2-mercaptoethanol prior to HF cleavage. Cleavage from the resin using HF/p-cresol gave the reduced thioester precursor peptide in good yield and purity, however RP-BPLC showed that this was accompanied by a small amount (approximately 5%) of oxidised product as detected by analytical RP-HPLC. The major peak was found to be consistent with that of the expected reduced peptide thioester with the His(Dnp) protecting group retained (calculated molecular weight=1945.9 Da; found=1944.6±0.8 Da).

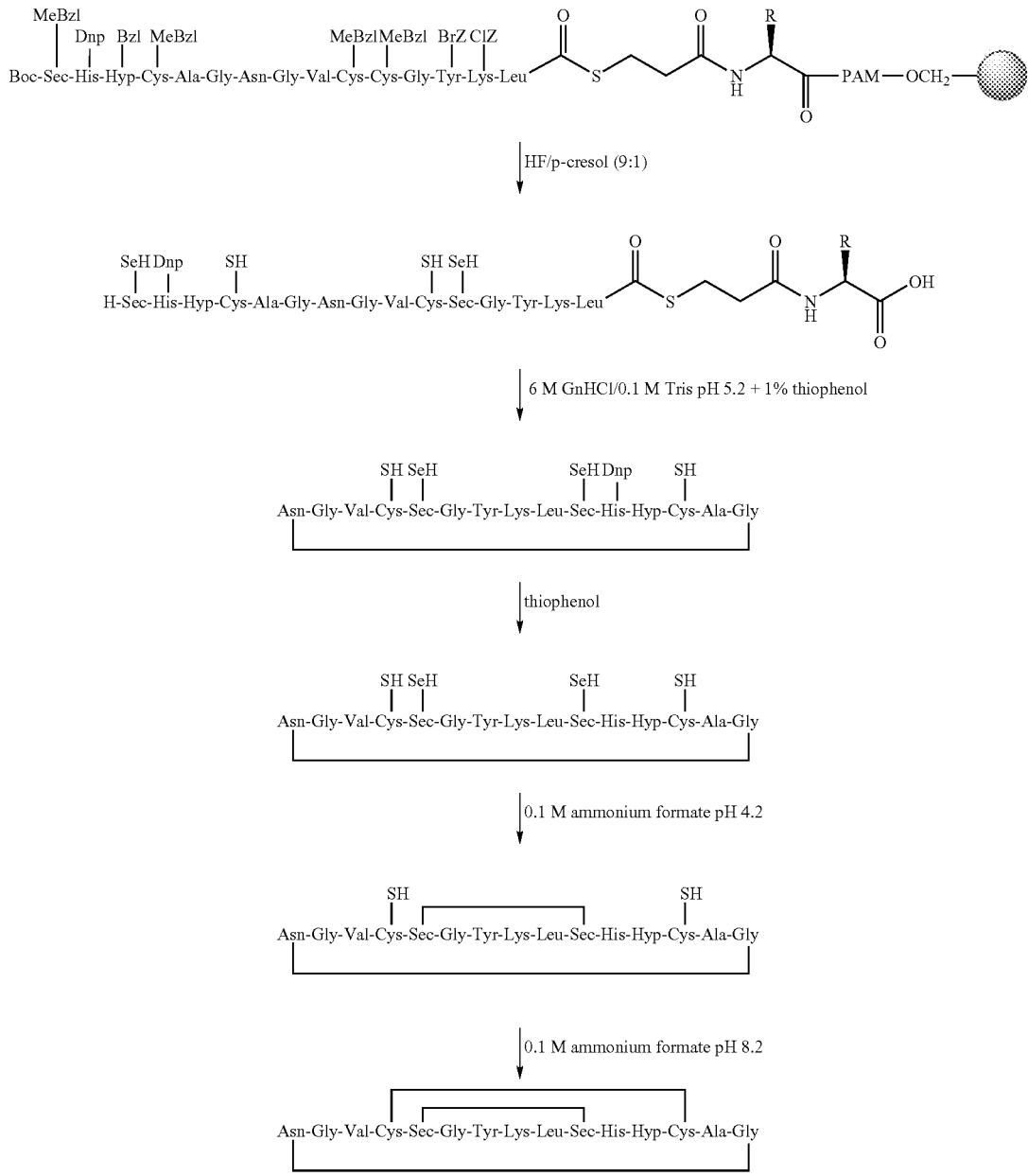

Scheme 2: Synthesis of [Sec5,10] cMrIA-AG (SEQ ID NO. 45 → SEQ ID NO. 47 → SEQ ID NO. 46 → SEQ ID NO. 46 → SEQ ID NO. 46 → SEQ ID NO. 46)

Transformation of linear thioester precursor to cyclic was performed by treatment in 6 M GnHCl/0.1 M tris buffer degassed with argon prior to use to ensure the transformation was performed in an inert atmosphere, which helped prevent unwanted oxidation. The inclusion of reducing agents is necessary to avoid rapid oxidation of selenocysteine to a diselenide bond. In the absence of reducing agents, diselenide bonds formation precluded the N-to-C cyclisation step, giving the diselenide thioester side product exclusively. The addition of 1% thiophenol was shown to be an effective reducing agent which also resulted in the simultaneous removal of His(Dnp) by thiolysis. Similar results were also obtained using 1% benzylmercaptan in a separate experiment. The reaction was carried out at pH 5 which is close to the pKa of selenocysteine (pKa=5.2), allowing deprotonation of the selenol moiety. The reaction was monitored by analytical RP-HPLC and was found to be complete after 7 hours, yielding a mixture of reduced and oxidised [Sec 5, 10]-cMrIA. Both products were isolated as a mixture and complete oxidation was achieved by oxidation in 0.1 M ammonium formate buffer, pH 4.2, followed by adjustment to pH 8.2 with ammonium hydroxide solution. A single product was isolated by semipreparative RP-HPLC in low yield (0.1 mg) and was found to correspond to the correct mass of the fully oxidised [Sec 5, 10]cMrIA-AG (m/z calculated 1612.57 Da, observed 1612.60±0.09 Da). The sequence of [Sec 5, 10]cMrIA-AG is as follows:

Asn Gly Val Cys Sec Gly Tyr Lys Leu Sec His Hyp Cys Ala Gly

SEQ ID NO. 17

(e) Radioligand Binding Assays

Cos-7 cells grown in 150 mm dishes containing DMEM and 10% serum, were transiently transfected with plasmid DNA encoding hNET using a metafectene reagent (Biontex). Membrane was prepared 48 hours post-transfection with the membrane stored in 10% glycerol at −80° C.

20 mM Tris (pH 7.4) containing 75 mM NaCl, 0.2 mM EDTA, 0.2 mM EGTA and 0.1% BSA was used a buffer. [N-methyl $^3$H] Nisoxetine HCl (Perkin Elmer Life Sciences, specific activity 70-87 Ci/mmol) was used at a concentration of 4.3 nM (approximate $k_D$ value). Initial concentration of competing ligand (MrIA analogues) were made at $3 \times 10^{-5}$ M (for a final concentration of $1 \times 10^{-5}$ M). 6×1:10 serial dilutions were then performed (50 µL top dose added to 450 µL buffer and repeated). 96 well polypropylene round-bottom natural assay plates (Medos) were used. 50 µL of each of competing compound, radioactive ligand and cell membrane were added successively to give a total assay volume of 150 µL and incubated at room temperature for 1 hour with shaking. The assay was harvested onto GF/B filtermats (Perkin Elmer Life Sciences) pre-treated with 0.6% PEI, using 3×0.8 mL/well of 20 mM HEPES pH 7.4; 125 mM NaCl at 4° C. Filtermats were dried, followed by addition of 9 mL betaplate scintillant and dispersed. The bags were then sealed and counted on a Microbeta counter fitted with 6 detectors. Each well was counted for 1 minute. Data was analysed using GraphPad Prism software.

The results are given in FIG. 11 and Table 5. These show that the introduction of the Selenocysteine into either native of cyclic MrIA results in no significant change in specific binding.

TABLE 5

Binding of χ-conotoxin MrIA analogues at the human NET expressed in Cos-7 cells,

| Analogue | log EC$_{50}$ | EC$_{50}$ |
| --- | --- | --- |
| [Sec5,10]MrIA-NH$_2$ | −5.86 | 1.38 ± 0.58 µM |
| [Sec5,10]cMrIA-AG | −5.67 | 2.14 ± 0.88 µM |

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A synthetically cyclised conotoxin peptide having an amide cyclised backbone such that the peptide has no free N- or C-terminus, said conotoxin peptide comprising at least two cysteine residues bonded to form a disulfide bond.

2. The cyclised conotoxin peptide according to claim 1 which contains or consists of the sequence of amino acids present in a naturally occurring conotoxin peptide.

3. The cyclised conotoxin peptide according to claim 2 wherein the naturally occurring conotoxin peptide is PVIIA (SEQ ID NO: 26), GS (SEQ ID NO: 37), GIIIA (SEQ ID NO: 33), GIIIB (SEQ ID NO: 34), GIIIC (SEQ ID NO: 35), PIIIA (SEQ ID NO: 36), MrIA (SEQ ID NO: 15) or Vc1.1 (SEQ ID NO: 13).

4. The cyclised conotoxin peptide according to claim 1 having three disulfide bonds in the form of a cystine knot.

5. The cyclised conotoxin peptide according to claim 1 comprising a linear conotoxin peptide and a peptide linker, wherein the N- and C-termini of the linear peptide are linked via the peptide linker to form the amide cyclised peptide backbone.

6. The cyclised conotoxin peptide according to claim 5 wherein the linear conotoxin peptide moiety comprises the sequence of a naturally occurring conotoxin peptide and the cyclised conotoxin peptide retains the disulfide bond connectivity of the naturally occurring conotoxin peptide.

7. The cyclised conotoxin peptide according to claim 5 wherein the peptide linker is from 2 to 15 amino acids in length.

8. The cyclised conotoxin peptide according to claim 5 wherein the peptide linker is selected from the group consisting of:

| | |
|---|---|
| TRNGLPG | SEQ ID NO: 1; |
| TRNG | SEQ ID NO: 2; |
| TRGGLPV | SEQ ID NO: 3; and |
| TNG | SEQ ID NO: 4. |

9. The cyclised conotoxin peptide according to claim 5 wherein the peptide linker comprises amino acids selected from the group consisting of glycine, alanine and combinations thereof.

10. The cyclised conotoxin peptide according to claim 1 wherein one or all of the disulfide bonds is substituted with a diselenium bond.

11. The cyclised conotoxin peptide according to claim 1 selected from the group consisting of:

Gly Cys Cys Ser Asn Pro Val Cys His Leu Glu His Ser Asn Leu Cys Gly Gly Ala Ala Gly Gly ⎦

SEQ ID NO: 11

Gly Cys Cys Ser Asn Pro Val Cys His Leu Glu His Ser Asn Leu Cys Gly Gly Ala Gly Ala Ala Gly ⎦

SEQ ID NO: 12

Gly Cys Cys Ser Asp Pro Arg Cys Asn Tyr Asp His Pro Glu Ile Cys Gly Gly Ala Ala Gly Gly ⎦

SEQ ID NO: 14

Asn Gly Val Cys Cys Gly Tyr Lys Leu Cys His Hyp Cys Ala Gly ⎦

SEQ ID NO: 16; and

Asn Gly Val Cys Sec Gly Tyr Lys Leu Sec His Hyp Cys Ala Gly ⎦

SEQ ID NO: 17.

12. A composition comprising the cyclised conotoxin peptide according to claim 1 and a pharmaceutically acceptable carrier or diluent.

13. The composition according to claim 12 which is a pharmaceutical composition.

14. A process for preparing the cyclised conotoxin according to claim 1 comprising:
(i) synthesising an extended linear conotoxin peptide on a solid phase support, said extended linear conotoxin peptide comprising a linear conotoxin peptide having a linker moiety attached to at least one end thereof,
(ii) cleaving said extended linear peptide from the support
(iii) cyclising said extended linear conotoxin peptide, and
(iv) oxidising said cyclised peptide to form disulfide bond(s).

15. A process for preparing the cyclic conotoxin according to claim 1 comprising:
(i) synthesising an extended linear conotoxin peptide on a solid phase support, said extended linear conotoxin peptide comprising a linear conotoxin peptide having a linker moiety attached to at least one end thereof,
(ii) cleaving said linear peptide from the solid support,
(iii) subjecting said extended peptide to conditions such that the peptide folds and forms the required disulfide bonds, and
(iv) cyclising the folded peptide.

16. A process for preparing the cyclic conotoxin according to claim 1 comprising:
(i) reacting a linear conotoxin peptide with a linker moiety to form an extended linear conotoxin peptide having said linker moiety attached to one end thereof,
(ii) cyclising said extended peptide and oxidizing to form disulfide bonds,
wherein said cyclising and oxidizing can be performed in any order.

17. A method for treating pain in a mammal comprising the step of administering to the mammal an amount of the cyclised conotoxin peptide of claim 1 effective to treat pain in the mammal.

18. A method for treating stroke in a mammal comprising the step of administering to the mammal an amount of the cyclised conotoxin peptide of claim 1 effective to treat stroke in the mammal.

19. A method for treating traumatic brain injury in a mammal comprising the step of administering to the mammal an amount of the cyclised conotoxin peptide of claim 1 effective to treat traumatic brain injury in the mammal.

20. A method of blocking a voltage-sensitive calcium channel in a mammal comprising administering to the mammal an amount of the cyclised conotoxin peptide according to claim 1 effective to block the voltage-sensitive calcium channel.

21. A method of blocking the nicotinic acetylcholine receptor in a mammal comprising administering to the mammal an amount of the cyclised conotoxin peptide according to claim 1 effective to block the nicotinic acetylcholine receptor.

22. A method of probing an ion channel receptor comprising contacting said ion channel receptor with the cyclised conotoxin peptide according to claim 1; and measuring a biological effect the cyclic conotoxin peptide has on the ion channel receptor.

23. A synthetically cyclised conotoxin peptide having an amide cyclised conotoxin such that the peptide has no free N- or C-terminus, said conotoxin peptide being a member of the A-superfamily and comprising four cysteine residues bonded in pairs to form two disulfide bonds, wherein the N-terminus of the corresponding linear/non-cyclised conotoxin peptide is linked to the C-terminus by a peptide linker such that between six and eight natural or unnatural amino acids span the distance between the first and the fourth cysteine residue.

24. A synthetically cyclised conotoxin peptide having an amide cyclised conotoxin peptide having an amide cyclised backbone such that the peptide has no free N- or C-terminus, said conotoxin peptide being a chi conotoxin peptide and comprising four cysteine residues bonded in pairs to form two disulfide bonds, wherein the N-terminus of the corresponding linear/non-cyclised conotoxin peptide is linked to the C-terminus by a peptide linker such that between four and six natural or unnatural amino acids span the distance between the first and the fourth cysteine residues.

* * * * *

UNITED STATES PATENT AND TRADEMARK OFFICE
CERTIFICATE OF CORRECTION

PATENT NO. : 7,312,195 B2
APPLICATION NO. : 11/052168
DATED : December 25, 2007
INVENTOR(S) : Craik et al.

It is certified that error appears in the above-identified patent and that said Letters Patent is hereby corrected as shown below:

Column 7, Table I, line 19, at "MII", please delete "GCCSNPBCHLEHSNLC" and insert -- GCCSNPVCHLEHSNLC -- therefor.

Claim 11, lines 3-12, please delete

" Gly Cys Cys Ser Asn Pro Val Cys His Leu Glu His Ser Asn Leu Cys Gly Gly Ala Ala Gly Gly
SEQ ID NO: 11
Gly Cys Cys Ser Asn Pro Val Cys His Leu Glu His Ser Asn Leu Cys Gly Gly Ala Gly Ala Ala Gly
SEQ ID NO: 12
Gly Cys Cys Ser Asp Pro Arg Cys Asn Tyr Asp His Pro Glu Ile Cys Gly Gly Ala Ala Gly Gly
SEQ ID NO: 14 "

UNITED STATES PATENT AND TRADEMARK OFFICE
CERTIFICATE OF CORRECTION

PATENT NO. : 7,312,195 B2  
APPLICATION NO. : 11/052168  
DATED : December 25, 2007  
INVENTOR(S) : Craik et al.

Page 2 of 2

It is certified that error appears in the above-identified patent and that said Letters Patent is hereby corrected as shown below:

and insert

Gly Cys Cys Ser Asn Pro Val Cys His Leu Glu His Ser Asn Leu Cys Gly Gly Ala Ala Gly Gly

--     SEQ ID NO: 11     --

Gly Cys Cys Ser Asn Pro Val Cys His Leu Glu His Ser Asn Leu Cys Gly Gly Ala Gly Ala Ala Gly

SEQ ID NO: 12

Gly Cys Cys Ser Asp Pro Arg Cys Asn Tyr Asp His Pro Glu Ile Cys Gly Gly Ala Ala Gly Gly

SEQ ID NO:14 therefor.

Signed and Sealed this

Seventh Day of April, 2009

JOHN DOLL  
*Acting Director of the United States Patent and Trademark Office*

SEQUENCE LISTING

```
<160> NUMBER OF SEQ ID NOS: 47

<210> SEQ ID NO 1
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1

Thr Arg Asn Gly Leu Pro Gly
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Thr Arg Asn Gly
1
```

<210> SEQ ID NO 3
<211> LENGTH: 7
<212> TYPE: PRT
<213> ORGANISM: Artificial Sequence
<220> FEATURE:
<223> OTHER INFORMATION: Synthetic Construct

<400> SEQUENCE: 3

Thr Arg Gly Gly Leu Pro Val
1               5

<210> SEQ ID NO 4
<211> LENGTH: 3
<212> TYPE: PRT
<213> ORGANISM: Artificial Sequence
<220> FEATURE:
<223> OTHER INFORMATION: Synthetic Construct

<400> SEQUENCE: 4

Thr Asn Gly
1

<210> SEQ ID NO 5
<211> LENGTH: 32
<212> TYPE: PRT
<213> ORGANISM: Artificial Sequence
<220> FEATURE:
<223> OTHER INFORMATION: Synthetic Construct

<400> SEQUENCE: 5

Cys Lys Gly Lys Gly Ala Lys Cys Ser Arg Leu Met Tyr Asp Cys Cys
1               5                   10                  15

Thr Gly Ser Cys Arg Ser Gly Lys Cys Thr Arg Asn Gly Leu Pro Gly
            20                  25                  30

<210> SEQ ID NO 6
<211> LENGTH: 29
<212> TYPE: PRT
<213> ORGANISM: Artificial Sequence
<220> FEATURE:
<223> OTHER INFORMATION: Synthetic Construct

<400> SEQUENCE: 6

Cys Lys Gly Lys Gly Ala Lys Cys Ser Arg Leu Met Tyr Asp Cys Cys
1               5                   10                  15

Thr Gly Ser Cys Arg Ser Gly Lys Cys Thr Arg Asn Gly
            20                  25

<210> SEQ ID NO 7
<211> LENGTH: 32
<212> TYPE: PRT
<213> ORGANISM: Artificial Sequence
<220> FEATURE:
<223> OTHER INFORMATION: Synthetic Construct

<400> SEQUENCE: 7

Gly Leu Pro Val Cys Lys Gly Lys Gly Ala Lys Cys Ser Arg Leu Met
1               5                   10                  15

Tyr Asp Cys Cys Thr Gly Ser Cys Arg Ser Gly Lys Cys Thr Arg Gly
            20                  25                  30

<210> SEQ ID NO 8
<211> LENGTH: 19
<212> TYPE: PRT

```
<213> ORGANISM: Artificial Sequence
<220> FEATURE:
<223> OTHER INFORMATION: Synthetic Construct

<400> SEQUENCE: 8

Gly Cys Cys Ser Asn Pro Val Cys His Leu Glu His Ser Asn Leu Cys
1               5                   10                  15

Thr Asn Gly

<210> SEQ ID NO 9
<211> LENGTH: 19
<212> TYPE: PRT
<213> ORGANISM: Artificial Sequence
<220> FEATURE:
<223> OTHER INFORMATION: Synthetic Construct

<400> SEQUENCE: 9

Cys Cys Ser Asn Pro Val Cys His Leu Glu His Ser Asn Leu Cys Thr
1               5                   10                  15

Asn Gly Gly

<210> SEQ ID NO 10
<211> LENGTH: 21
<212> TYPE: PRT
<213> ORGANISM: Artificial Sequence
<220> FEATURE:
<223> OTHER INFORMATION: Synthetic Construct

<400> SEQUENCE: 10

Gly Cys Cys Ser Asn Pro Val Cys His Leu Glu His Ser Asn Leu Cys
1               5                   10                  15

Gly Gly Ala Ala Gly
                20

<210> SEQ ID NO 11
<211> LENGTH: 22
<212> TYPE: PRT
<213> ORGANISM: Artificial Sequence
<220> FEATURE:
<223> OTHER INFORMATION: Synthetic Construct

<400> SEQUENCE: 11

Gly Cys Cys Ser Asn Pro Val Cys His Leu Glu His Ser Asn Leu Cys
1               5                   10                  15

Gly Gly Ala Ala Gly Gly
                20

<210> SEQ ID NO 12
<211> LENGTH: 23
<212> TYPE: PRT
<213> ORGANISM: Artificial Sequence
<220> FEATURE:
<223> OTHER INFORMATION: Synthetic Construct

<400> SEQUENCE: 12

Gly Cys Cys Ser Asn Pro Val Cys His Leu Glu His Ser Asn Leu Cys
1               5                   10                  15

Gly Gly Ala Gly Ala Ala Gly
                20

<210> SEQ ID NO 13
<211> LENGTH: 16
<212> TYPE: PRT
<213> ORGANISM: Conus victoriae
```

-continued

```
<400> SEQUENCE: 13

Gly Cys Cys Ser Asp Pro Arg Cys Asn Tyr Asp His Pro Glu Ile Cys
1               5                   10                  15

<210> SEQ ID NO 14
<211> LENGTH: 22
<212> TYPE: PRT
<213> ORGANISM: Artificial Sequence
<220> FEATURE:
<223> OTHER INFORMATION: Synthetic Construct

<400> SEQUENCE: 14

Gly Cys Cys Ser Asp Pro Arg Cys Asn Tyr Asp His Pro Glu Ile Cys
1               5                   10                  15

Gly Gly Ala Ala Gly Gly
            20

<210> SEQ ID NO 15
<211> LENGTH: 13
<212> TYPE: PRT
<213> ORGANISM: Conus marmoreus
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 15

Asn Gly Val Cys Cys Gly Tyr Lys Leu Cys His Xaa Cys
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 16

Asn Gly Val Cys Cys Gly Tyr Lys Leu Cys His Xaa Cys Ala Gly
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is selenocysteine
<220> FEATURE:
<221> NAME/KEY: MISC_FEATURE
<222> LOCATION: (10)..(10)
<223> OTHER INFORMATION: Xaa is selenocysteine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 17

Asn Gly Val Cys Xaa Gly Tyr Lys Leu Xaa His Xaa Cys Ala Gly
1               5                   10                  15
```

```
<210> SEQ ID NO 18
<211> LENGTH: 25
<212> TYPE: PRT
<213> ORGANISM: Conus magus

<400> SEQUENCE: 18

Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25

<210> SEQ ID NO 19
<211> LENGTH: 26
<212> TYPE: PRT
<213> ORGANISM: Conus magus
<220> FEATURE:
<221> NAME/KEY: MISC_FEATURE
<222> LOCATION: (7)..(7)
<223> OTHER INFORMATION: Xaa = 4-hydroxproline

<400> SEQUENCE: 19

Cys Lys Gly Lys Gly Ala Xaa Cys Arg Lys Thr Met Tyr Asp Cys Cys
1               5                   10                  15

Ser Gly Ser Cys Gly Arg Arg Gly Lys Cys
            20                  25

<210> SEQ ID NO 20
<211> LENGTH: 27
<212> TYPE: PRT
<213> ORGANISM: Conus geographus
<220> FEATURE:
<221> NAME/KEY: MISC_FEATURE
<222> LOCATION: (4)..(4)
<223> OTHER INFORMATION: Xaa = 4-hydroxproline
<220> FEATURE:
<221> NAME/KEY: MISC_FEATURE
<222> LOCATION: (10)..(10)
<223> OTHER INFORMATION: Xaa = 4-hydroxproline
<220> FEATURE:
<221> NAME/KEY: MISC_FEATURE
<222> LOCATION: (21)..(21)
<223> OTHER INFORMATION: Xaa = 4-hydroxproline

<400> SEQUENCE: 20

Cys Lys Ser Xaa Gly Ser Ser Cys Ser Xaa Thr Ser Tyr Asn Cys Cys
1               5                   10                  15

Arg Ser Cys Asn Xaa Tyr Thr Lys Arg Cys Tyr
            20                  25

<210> SEQ ID NO 21
<211> LENGTH: 24
<212> TYPE: PRT
<213> ORGANISM: Conus striatus
<220> FEATURE:
<221> NAME/KEY: MISC_FEATURE
<222> LOCATION: (7)..(7)
<223> OTHER INFORMATION: Xaa = 4-hydroxproline

<400> SEQUENCE: 21

Cys Arg Ser Ser Gly Ser Xaa Cys Gly Val Thr Ser Ile Cys Cys Gly
1               5                   10                  15

Arg Cys Tyr Arg Gly Lys Cys Thr
            20

<210> SEQ ID NO 22
<211> LENGTH: 26
```

```
<212> TYPE: PRT
<213> ORGANISM: Conus striatus

<400> SEQUENCE: 22

Cys Lys Leu Lys Gly Gln Ser Cys Arg Lys Thr Ser Tyr Asp Cys Cys
1               5                   10                  15

Ser Gly Ser Cys Gly Arg Ser Gly Lys Cys
            20                  25

<210> SEQ ID NO 23
<211> LENGTH: 29
<212> TYPE: PRT
<213> ORGANISM: Conus geographus
<220> FEATURE:
<221> NAME/KEY: MISC_FEATURE
<222> LOCATION: (4)..(4)
<223> OTHER INFORMATION: Xaa = 4-hydroxproline
<220> FEATURE:
<221> NAME/KEY: MISC_FEATURE
<222> LOCATION: (7)..(7)
<223> OTHER INFORMATION: Xaa = 4-hydroxproline

<400> SEQUENCE: 23

Cys Lys Ser Xaa Gly Thr Xaa Cys Ser Arg Gly Met Arg Asp Cys Cys
1               5                   10                  15

Thr Ser Cys Leu Leu Tyr Ser Asn Lys Cys Arg Arg Tyr
            20                  25

<210> SEQ ID NO 24
<211> LENGTH: 29
<212> TYPE: PRT
<213> ORGANISM: Conus geographus
<220> FEATURE:
<221> NAME/KEY: MISC_FEATURE
<222> LOCATION: (4)..(4)
<223> OTHER INFORMATION: Xaa = 4-hydroxproline
<220> FEATURE:
<221> NAME/KEY: MISC_FEATURE
<222> LOCATION: (7)..(7)
<223> OTHER INFORMATION: Xaa = 4-hydroxproline

<400> SEQUENCE: 24

Cys Lys Ser Xaa Gly Thr Xaa Cys Ser Arg Gly Met Arg Asp Cys Cys
1               5                   10                  15

Thr Ser Cys Leu Ser Tyr Ser Asn Lys Cys Arg Arg Tyr
            20                  25

<210> SEQ ID NO 25
<211> LENGTH: 27
<212> TYPE: PRT
<213> ORGANISM: Conus tulipa
<220> FEATURE:
<221> NAME/KEY: MISC_FEATURE
<222> LOCATION: (4)..(4)
<223> OTHER INFORMATION: Xaa = 4-hydroxproline
<220> FEATURE:
<221> NAME/KEY: MISC_FEATURE
<222> LOCATION: (10)..(10)
<223> OTHER INFORMATION: Xaa = 4-hydroxproline
<220> FEATURE:
<221> NAME/KEY: MISC_FEATURE
<222> LOCATION: (21)..(21)
<223> OTHER INFORMATION: Xaa = 4-hydroxproline

<400> SEQUENCE: 25

Cys Leu Ser Xaa Gly Ser Ser Cys Ser Xaa Thr Ser Tyr Asn Cys Cys
1               5                   10                  15

Arg Ser Cys Asn Xaa Tyr Ser Arg Lys Cys Arg
            20                  25
```

```
                        20                  25

<210> SEQ ID NO 26
<211> LENGTH: 27
<212> TYPE: PRT
<213> ORGANISM: Conus purpurascens
<220> FEATURE:
<221> NAME/KEY: MISC_FEATURE
<222> LOCATION: (4)..(4)
<223> OTHER INFORMATION: Xaa = 4-hydroxproline

<400> SEQUENCE: 26

Cys Arg Ile Xaa Asn Gln Lys Cys Phe Gln His Leu Asp Asp Cys Cys
1               5                   10                  15

Ser Arg Lys Cys Asn Arg Phe Asn Lys Cys Val
            20                  25

<210> SEQ ID NO 27
<211> LENGTH: 13
<212> TYPE: PRT
<213> ORGANISM: Conus geographus

<400> SEQUENCE: 27

Glu Cys Cys Asn Pro Ala Cys Gly Arg His Tyr Ser Cys
1               5                   10

<210> SEQ ID NO 28
<211> LENGTH: 12
<212> TYPE: PRT
<213> ORGANISM: Conus imperialis

<400> SEQUENCE: 28

Gly Cys Cys Ser Asp Pro Arg Cys Ala Trp Arg Cys
1               5                   10

<210> SEQ ID NO 29
<211> LENGTH: 16
<212> TYPE: PRT
<213> ORGANISM: Conus pennaceus

<400> SEQUENCE: 29

Gly Cys Cys Ser Leu Pro Pro Cys Ala Ala Asn Asn Pro Asp Tyr Cys
1               5                   10                  15

<210> SEQ ID NO 30
<211> LENGTH: 16
<212> TYPE: PRT
<213> ORGANISM: Conus pennaceus

<400> SEQUENCE: 30

Asx Cys Cys Ser Leu Pro Pro Cys Ala Leu Ser Asn Pro Asp Tyr Cys
1               5                   10                  15

<210> SEQ ID NO 31
<211> LENGTH: 19
<212> TYPE: PRT
<213> ORGANISM: Conus striatus

<400> SEQUENCE: 31

Gly Cys Cys Cys Asn Pro Ala Cys Gly Pro Asn Tyr Gly Cys Gly Thr
1               5                   10                  15

Ser Cys Ser

<210> SEQ ID NO 32
```

```
<211> LENGTH: 16
<212> TYPE: PRT
<213> ORGANISM: Conus magus

<400> SEQUENCE: 32

Gly Cys Cys Ser Asn Pro Asx Cys His Leu Glu His Ser Asn Leu Cys
1               5                   10                  15

<210> SEQ ID NO 33
<211> LENGTH: 22
<212> TYPE: PRT
<213> ORGANISM: Conus geographus
<220> FEATURE:
<221> NAME/KEY: MISC_FEATURE
<222> LOCATION: (6)..(7)
<223> OTHER INFORMATION: Xaa = 4-hydroxproline
<220> FEATURE:
<221> NAME/KEY: MISC_FEATURE
<222> LOCATION: (17)..(17)
<223> OTHER INFORMATION: Xaa = 4-hydroxproline

<400> SEQUENCE: 33

Arg Asp Cys Cys Thr Xaa Xaa Lys Lys Cys Lys Asp Arg Gln Cys Lys
1               5                   10                  15

Xaa Gln Arg Cys Cys Ala
            20

<210> SEQ ID NO 34
<211> LENGTH: 22
<212> TYPE: PRT
<213> ORGANISM: Conus geographus
<220> FEATURE:
<221> NAME/KEY: MISC_FEATURE
<222> LOCATION: (6)..(7)
<223> OTHER INFORMATION: Xaa = 4-hydroxproline
<220> FEATURE:
<221> NAME/KEY: MISC_FEATURE
<222> LOCATION: (17)..(17)
<223> OTHER INFORMATION: Xaa = 4-hydroxproline

<400> SEQUENCE: 34

Arg Asp Cys Cys Thr Xaa Xaa Arg Lys Cys Lys Asp Arg Arg Cys Lys
1               5                   10                  15

Xaa Met Lys Cys Cys Ala
            20

<210> SEQ ID NO 35
<211> LENGTH: 22
<212> TYPE: PRT
<213> ORGANISM: Conus geographus
<220> FEATURE:
<221> NAME/KEY: MISC_FEATURE
<222> LOCATION: (6)..(7)
<223> OTHER INFORMATION: Xaa = 4-hydroxproline
<220> FEATURE:
<221> NAME/KEY: MISC_FEATURE
<222> LOCATION: (17)..(17)
<223> OTHER INFORMATION: Xaa = 4-hydroxproline

<400> SEQUENCE: 35

Arg Asp Cys Cys Thr Xaa Xaa Lys Lys Cys Lys Asp Arg Arg Cys Lys
1               5                   10                  15

Xaa Leu Lys Cys Cys Ala
            20

<210> SEQ ID NO 36
<211> LENGTH: 22
<212> TYPE: PRT
```

```
<213> ORGANISM: Conus purpurascens
<220> FEATURE:
<221> NAME/KEY: MISC_FEATURE
<222> LOCATION: (8)..(8)
<223> OTHER INFORMATION: Xaa = 4-hydroxproline
<220> FEATURE:
<221> NAME/KEY: MISC_FEATURE
<222> LOCATION: (18)..(18)
<223> OTHER INFORMATION: Xaa = 4-hydroxproline

<400> SEQUENCE: 36

Glx Arg Leu Cys Cys Gly Phe Xaa Lys Ser Cys Arg Ser Arg Gln Cys
1               5                   10                  15

Lys Xaa His Arg Cys Cys
            20

<210> SEQ ID NO 37
<211> LENGTH: 34
<212> TYPE: PRT
<213> ORGANISM: Conus geographus

<400> SEQUENCE: 37

Ala Cys Ser Gly Arg Gly Ser Arg Cys Pro Pro Gln Cys Cys Met Gly
1               5                   10                  15

Leu Arg Cys Gly Arg Gly Asn Pro Gln Lys Cys Ile Gly Ala His Glu
            20                  25                  30

Asp Val

<210> SEQ ID NO 38
<211> LENGTH: 4
<212> TYPE: PRT
<213> ORGANISM: Artificial Sequence
<220> FEATURE:
<223> OTHER INFORMATION: Synthetic Construct

<400> SEQUENCE: 38

Gly Leu Pro Val
1

<210> SEQ ID NO 39
<211> LENGTH: 3
<212> TYPE: PRT
<213> ORGANISM: Artificial Sequence
<220> FEATURE:
<223> OTHER INFORMATION: Synthetic Construct

<400> SEQUENCE: 39

Thr Arg Gly
1

<210> SEQ ID NO 40
<211> LENGTH: 5
<212> TYPE: PRT
<213> ORGANISM: Artificial Sequence
<220> FEATURE:
<223> OTHER INFORMATION: Synthetic Construct

<400> SEQUENCE: 40

Gly Gly Ala Ala Gly
1               5

<210> SEQ ID NO 41
<211> LENGTH: 6
<212> TYPE: PRT
<213> ORGANISM: Artificial Sequence
<220> FEATURE:
```

-continued

<223> OTHER INFORMATION: Synthetic Construct

<400> SEQUENCE: 41

Gly Gly Ala Ala Gly Gly
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic Construct

<400> SEQUENCE: 42

Gly Gly Ala Gly Ala Ala Gly
1               5

<210> SEQ ID NO 43
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is 4-hydroxyproline

<400> SEQUENCE: 43

Cys His Xaa Cys Ala Gly Asn Gly Val Cys Cys Gly Tyr Lys Leu
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 44

Asn Gly Val Cys Cys Gly Tyr Lys Leu Cys His Xaa Cys Ala Gly
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is selenocysteine
<220> FEATURE:
<221> NAME/KEY: MISC_FEATURE
<222> LOCATION: (3)..(3)
<223> OTHER INFORMATION: Xaa is 4-hydroxyproline

<400> SEQUENCE: 45

Xaa His Xaa Cys Ala Gly Asn Gly Val Cys Cys Gly Tyr Lys Leu
1               5                   10                  15

<210> SEQ ID NO 46
<211> LENGTH: 15
<212> TYPE: PRT

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is selenocysteine
<220> FEATURE:
<221> NAME/KEY: MISC_FEATURE
<222> LOCATION: (10)..(10)
<223> OTHER INFORMATION: Xaa is selenocysteine
<220> FEATURE:
<221> NAME/KEY: MISC_FEATURE
<222> LOCATION: (12)..(12)
<223> OTHER INFORMATION: Xaa is 4-hydroxyproline

<400> SEQUENCE: 46

Asn Gly Val Cys Xaa Gly Tyr Lys Leu Xaa His Xaa Cys Ala Gly
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is selenocysteine
<220> FEATURE:
<221> NAME/KEY: MISC_FEATURE
<222> LOCATION: (3)..(3)
<223> OTHER INFORMATION: Xaa is 4-hydroxyproline
<220> FEATURE:
<221> NAME/KEY: MISC_FEATURE
<222> LOCATION: (11)..(11)
<223> OTHER INFORMATION: Xaa is selenocysteine

<400> SEQUENCE: 47

Xaa His Xaa Cys Ala Gly Asn Gly Val Cys Xaa Gly Tyr Lys Leu
1               5                   10                  15
```